US010214553B2

(12) United States Patent
Albrecht et al.

(10) Patent No.: US 10,214,553 B2
(45) Date of Patent: Feb. 26, 2019

(54) SOLID STATE FORMS OF SOFOSBUVIR

(71) Applicants: ratiopharm GmbH, Ulm (DE); Teva Pharmaceuticals International GmbH, Jona (CH)

(72) Inventors: Wolfgang Albrecht, Ulm (DE); Judith Aronhime, Rehovot (IL); Brijnath P. Chaurasia, Uttar Pradesh (IN); Jens Geier, Hayingen (DE); Richard Guserle, Koetz (DE); Julia Hrakovsky, Rosh Ha-Ayin (IL); Claudia Lauer, Gauting (DE); Ramkaran Prajapati, Haryana (IN); Vinod K. Kansal, Haryana (IN); Pavan V. Kumar, Andhra Pradesh (IN); Hans-Juergen Mika, Bonn (DE); Siva Rama Krishna Muppalla, Gajraula:UP (IN); Marina Ratkaj, Zagreb (HR); Roman Safonov, Petah-Tikva (IL); Dirk Schenk, Munich (DE); Naveen C. Srivastav, Uttar Pradesh (IN); Ralph Stefan, Ebenweiler (DE); Ashish Tripathi, Uttar Pradesh (IN)

(73) Assignees: TEVA PHARMACEUTICALS INTERNATIONAL GMBH, Jona (CH); RATIOPHARM GMBH, Ulm (DE)

( * ) Notice: Subject to any disclaimer, the term of this patent is extended or adjusted under 35 U.S.C. 154(b) by 0 days.

(21) Appl. No.: 15/318,385

(22) PCT Filed: Jun. 12, 2015

(86) PCT No.: PCT/US2015/035457
§ 371 (c)(1),
(2) Date: Dec. 13, 2016

(87) PCT Pub. No.: WO2015/191945
PCT Pub. Date: Dec. 17, 2015

(65) Prior Publication Data

US 2017/0137453 A1 May 18, 2017

Related U.S. Application Data

(60) Provisional application No. 62/157,043, filed on May 5, 2015, provisional application No. 62/119,599, filed on Feb. 23, 2015.

(30) Foreign Application Priority Data

| | | |
|---|---|---|
| Jun. 13, 2014 | (IN) | 1610/DEL/2014 |
| Jul. 3, 2014 | (EP) | 14002279 |
| Aug. 7, 2014 | (EP) | 14180278 |
| Aug. 8, 2014 | (IN) | 2268/DEL/2014 |
| May 11, 2015 | (EP) | 15167228 |
| May 13, 2015 | (EP) | 15167683 |
| May 14, 2015 | (IN) | 1348/DEL/2015 |
| May 29, 2015 | (EP) | 15169888 |

(51) Int. Cl.
*C07H 19/06* (2006.01)
*A61K 31/7072* (2006.01)
*A61K 9/20* (2006.01)
*A61K 31/4184* (2006.01)

(52) U.S. Cl.
CPC .......... *C07H 19/06* (2013.01); *A61K 9/2009* (2013.01); *A61K 9/2054* (2013.01); *A61K 31/4184* (2013.01); *A61K 31/7072* (2013.01); *C07B 2200/13* (2013.01)

(58) Field of Classification Search
CPC .......................... C07H 19/06; A61K 31/7072
See application file for complete search history.

(56) References Cited

U.S. PATENT DOCUMENTS

| | | | | |
|---|---|---|---|---|
| 7,964,580 B2 | 6/2011 | Sofia et al. | | |
| 8,236,779 B2 * | 8/2012 | Ma | C07H 19/067 514/50 | |
| 8,334,270 B2 | 12/2012 | Sofia et al. | | |
| 8,618,076 B2 | 12/2013 | Ross et al. | | |
| 8,629,263 B2 | 1/2014 | Ross et al. | | |
| 8,633,309 B2 | 1/2014 | Ross et al. | | |
| 8,642,756 B2 | 2/2014 | Ross et al. | | |
| 8,735,569 B2 | 5/2014 | Ross et al. | | |
| 8,889,159 B2 * | 11/2014 | Cleary | A61K 9/2009 424/400 | |
| 9,206,217 B2 | 12/2015 | Ross et al. | | |
| 9,284,342 B2 | 3/2016 | Ross et al. | | |
| 9,340,568 B2 | 5/2016 | Casteel et al. | | |
| 9,549,941 B2 | 1/2017 | Cleary et al. | | |
| 9,637,512 B2 | 5/2017 | Chun et al. | | |
| 2011/0251152 A1 | 10/2011 | Ross et al. | | |
| 2016/0354400 A1 | 12/2016 | Ross et al. | | |
| 2017/0015696 A1 * | 1/2017 | Palacios | C07H 19/06 | |

FOREIGN PATENT DOCUMENTS

| | | |
|---|---|---|
| WO | 2008/121634 | 10/2008 |
| WO | 2010/135569 A1 | 11/2010 |
| WO | 2011/123645 A2 | 10/2011 |
| WO | 2011/123668 | 10/2011 |
| WO | 2011/123672 A1 | 10/2011 |
| WO | 2013/082003 A1 | 6/2013 |
| WO | 2014/008236 | 1/2014 |
| WO | 2015/097605 | 7/2015 |
| WO | 2015/099989 A1 | 7/2015 |

(Continued)

OTHER PUBLICATIONS

Singhal et al., Adv. Drug Delivery Rev., 2004, 56, p. 335-347. (Year: 2004).*

(Continued)

*Primary Examiner* — Jonathan S Lau
(74) *Attorney, Agent, or Firm* — Baker & Hostetler LLP

(57) ABSTRACT

The present disclosure encompasses solid state forms of Sofosbuvir, processes for their production, and pharmaceutical compositions thereof.

24 Claims, 13 Drawing Sheets

(56) References Cited

FOREIGN PATENT DOCUMENTS

| WO | 2015/132321 | 9/2015 |
|---|---|---|
| WO | 2015/150561 | 10/2015 |
| WO | 2016/008461 | 1/2016 |
| WO | 2016/016327 | 2/2016 |
| WO | 2016/016447 | 2/2016 |
| WO | 2016/023905 | 2/2016 |
| WO | 2016/023906 | 2/2016 |
| WO | 2016/035006 | 3/2016 |
| WO | 2016/038542 | 3/2016 |
| WO | 2016/055576 | 4/2016 |
| WO | 2016/097173 | 6/2016 |
| WO | 2016/156512 | 10/2016 |
| WO | 2016/189443 | 12/2016 |
| WO | 2017/158624 | 9/2017 |

OTHER PUBLICATIONS

Sofia et al. "Discovery of a beta-D-2-Deoxy-2-alpha-fluoro-2-beta-C-methyluridine Nucleotide Prod rug for the Treatment of Hepatitis C Virus", Journal of Medicinal Chemistry, vol. 53, No. 19, pp. 7202-7218, Sep. 2010.

Caira, "Crystalline Polymorphism of Organic Compounds", Topics in Current Chemistry, Springer, Berlin, DE, vol. 198, pp. 163-208, Jan. 1998.

\* cited by examiner

Figure 1: X-ray powder diffractogram of Form E of Sofosbuvir

Figure 2: X-ray powder diffractogram of Form 1 of Sofosbuvir.

Figure 9: X-ray powder pattern of Sofosbuvir Form 7

| Angle °(2θ) | d value Ångström | Intensity % |
|---|---|---|
| 8.10 | 10.90138 | 55.4 |
| 10.39 | 8.50521 | 29.2 |
| 12.11 | 7.30055 | 13.8 |
| 12.44 | 7.11131 | 91.6 |
| 13.48 | 6.56585 | 16.5 |
| 16.22 | 5.45921 | 14.5 |
| 16.82 | 5.26578 | 38.4 |
| 17.22 | 5.14499 | 100 |
| 18.01 | 4.92142 | 21.1 |
| 18.69 | 4.74427 | 22.4 |
| 19.40 | 4.57274 | 90.3 |
| 20.05 | 4.42616 | 85.1 |
| 20.85 | 4.25772 | 43.7 |
| 21.41 | 4.14654 | 5 |
| 21.84 | 4.06646 | 6 |
| 22.02 | 4.03407 | 13.2 |
| 23.32 | 3.81201 | 26.2 |
| 23.66 | 3.75736 | 19.8 |
| 24.39 | 3.64701 | 8.2 |
| 24.94 | 3.56688 | 22.9 |
| 25.33 | 3.51338 | 28 |
| 27.15 | 3.28186 | 28.8 |
| 27.99 | 3.18501 | 23.5 |
| 28.58 | 3.12131 | 13.8 |
| 29.04 | 3.07199 | 5.3 |
| 29.64 | 3.01165 | 9.2 |
| 31.29 | 2.85663 | 19.3 |
| 32.00 | 2.79485 | 9.5 |
| 32.75 | 2.7325 | 8.4 |
| 33.16 | 2.69957 | 7.7 |
| 33.44 | 2.67786 | 6.5 |
| 35.07 | 2.55668 | 9.6 |
| 35.89 | 2.50039 | 3.6 |
| 36.83 | 2.43842 | 6.8 |
| 37.90 | 2.37192 | 10.2 |
| 38.25 | 2.35128 | 7.1 |
| 39.21 | 2.29598 | 9.9 |
| 40.98 | 2.20064 | 8.7 |
| 42.05 | 2.14706 | 5.5 |
| 42.45 | 2.12796 | 9.1 |
| 44.47 | 2.03552 | 7.7 |
| 44.83 | 2.01994 | 7.2 |
| 46.12 | 1.96674 | 2.9 |
| 48.87 | 1.86228 | 2.7 |
| 49.63 | 1.83553 | 3 |
| 51.41 | 1.77591 | 6.2 |
| 52.31 | 1.74755 | 6 |
| 53.76 | 1.70382 | 5.4 |

Figure 11 – X-Ray Powder diffraction listings for Form 7

| Angle [° 2Θ] | Relative Intensity |
|---|---|
| 6.2 | 0.5% |
| 8.1 | 56% |
| 10.4 | 26% |
| 12.1 | 11% |
| 12.4 | 100% |
| 13.5 | 16% |
| 16.2 | 13% |
| 16.8 | 28% |
| 17.2 | 41% |
| 18.0 | 8% |
| 18.7 | 24% |
| 19.4 | 75% |
| 20.0 | 55% |
| 20.9 | 37% |
| 21.4 | 5% |
| 21.8 | 3% |
| 22.0 | 8% |
| 23.1 | 5% |
| 23.3 | 15% |
| 23.6 | 12% |
| 24.4 | 6% |
| 24.9 | 14% |
| 25.3 | 18% |
| 25.5 | 10% |
| 27.2 | 20% |
| 28.0 | 15% |
| 28.1 | 11% |
| 28.6 | 8% |
| 29.0 | 5% |
| 29.6 | 7% |
| 31.3 | 12% |
| 32.0 | 6% |
| 32.3 | 7% |
| 32.8 | 6% |
| 33.1 | 6% |
| 33.4 | 5% |
| 34.7 | 4% |
| 35.1 | 6% |
| 35.9 | 1% |
| 36.8 | 4% |
| 37.2 | 3% |
| 37.9 | 8% |
| 38.2 | 5% |
| 39.2 | 6% |
| 39.4 | 6% |
| 40.6 | 4% |
| 41.0 | 6% |
| 42.0 | 4% |
| 42.4 | 6% |
| 43.6 | 2% |
| 44.5 | 6% |
| 44.8 | 4% |

Figure 12 – X-Ray Powder diffraction listings for Form 1

| Angle [° 2Θ] | Relative Intensity |
|---|---|
| 4.1 | 1% |
| 4.8 | 8% |
| 5.0 | 100% |
| 7.3 | 60% |
| 7.8 | 2% |
| 8.2 | 5% |
| 8.8 | 5% |
| 9.4 | 15% |
| 10.0 | 8% |
| 11.4 | 3% |
| 11.6 | 1% |
| 12.4 | 1% |
| 13.2 | 2% |
| 14.2 | 4% |
| 14.7 | 1% |
| 15.0 | 4% |
| 15.1 | 1% |
| 16.1 | 5% |
| 16.4 | 10% |
| 16.5 | 10% |
| 16.8 | 1% |
| 17.3 | 14% |
| 17.6 | 6% |
| 18.1 | 24% |
| 18.4 | 6% |
| 18.7 | 10% |
| 18.9 | 5% |
| 19.3 | 7% |
| 19.5 | 2% |
| 20.2 | 6% |
| 20.5 | 10% |
| 20.7 | 3% |
| 21.2 | 1% |
| 21.8 | 5% |
| 22.0 | 11% |
| 22.3 | 9% |
| 22.8 | 2% |
| 23.2 | 5% |
| 23.3 | 6% |
| 23.5 | 5% |
| 23.7 | 6% |
| 24.0 | 3% |
| 24.7 | 3% |
| 25.0 | 12% |
| 25.5 | 2% |
| 26.5 | 4% |
| 27.1 | 4% |
| 27.1 | 4% |
| 27.2 | 3% |
| 27.4 | 2% |
| 28.1 | 3% |
| 28.5 | 1% |
| 28.9 | 2% |
| 29.3 | 1% |
| 30.0 | 2% |
| 30.5 | 1% |
| 31.0 | 2% |
| 31.5 | 2% |

SOLID STATE FORMS OF SOFOSBUVIR

CROSS REFERENCE TO RELATED APPLICATIONS

This application is the National Stage Application of International Patent Application No. PCT/US2015/035457, filed Jun. 12, 2015, which claims the benefit of Indian Application No. 1610/DEL/2014, filed Jun. 13, 2014; European Application No. 14002279.9, filed Jul. 3, 2014; European Application No. 14180278.5, filed Aug. 7, 2014; Indian Application No. 2268/DEL/2014, filed Aug. 8, 2014; U.S. Provisional Application No. 62/119,599, filed Feb. 23, 2015; U.S. Provisional Application No. 62/157,043, filed May 5, 2015, European Application No. 15167228.4, filed May 11, 2015; European Application No. 15167683.0, filed May 13, 2015; Indian Application No. 1348/DEL/2015, filed May 14, 2015; European Application No. 15169888.3, filed May 29, 2015, the entireties of which are incorporated herein by reference.

FIELD OF THE INVENTION

The present invention encompasses solid state forms of Sofosbuvir, processes for their production and pharmaceutical compositions thereof.

BACKGROUND OF THE INVENTION

Sofosbuvir, L-Alanine, N-[[P(S),2'R]-2'-deoxy-2'-fluoro-2'-methyl-P-phenyl-5'-uridylyl]-, 1-methylethyl ester, or (2S)-isopropyl 2-(((((2R,3R,4R,5R)-5-(2,4-dioxo-3,4-dihydropyrimidin-1(2H)-yl)-4-fluoro-3-hydroxy-4-methyltetrahydrofuran-2-yl)methoxy)(phenoxy)phosphoryl)amino)propanoate, having the following formula,

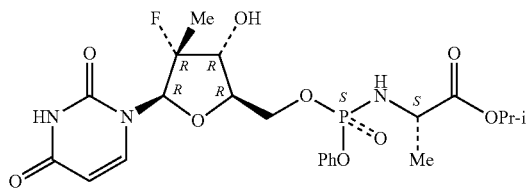

is an orally available, second generation uridine nucleoside analogue which inhibits the NS-5 protein of hepatitis C virus (HCV). Sofosbuvir and its isomer act as prodrugs and are converted through a series of in vivo transformations to an active triphosphate metabolite.

Sofosbuvir is marketed under the registered trademark SOVALDI®. SOVALDI® is available as immediate release tablets. Each tablet contains 400 mg of sofosbuvir. The active ingredient load in SOVALDI® tablets is about 30% and the tablets also contains glidant. More specifically, the SOVALDI® tablets include the following inactive ingredients: colloidal silicon dioxide, croscarmellose sodium, magnesium stearate, mannitol, and microcrystalline cellulose. The tablets are film-coated with a coating material containing the following inactive ingredients: polyethylene glycol, polyvinyl alcohol, talc, titanium dioxide, and yellow iron oxide. WO 2013/082003 and WO 2014/120981 also describes tablets containing sofosbuvir.

Sofosbuvir is described in U.S. Pat. No. 7,964,580 and in U.S. Pat. No. 8,334,270. Solid state forms of Sofosbuvir are described in WO 2010/135569, US 2011/251152, WO 2011/123645 and CN 104130302. CN 104277088 and CN 104447924 also describe crystalline forms of sofosbuvir.

Polymorphism, the occurrence of different crystalline forms, is a property of some molecules and molecular complexes. A single molecule may give rise to a variety of polymorphs having distinct crystal structures and physical properties like melting point, thermal behaviors (e.g. measured by thermogravimetric analysis—"TGA," or differential scanning calorimetry—"DSC"), X-ray diffraction pattern, infrared absorption fingerprint, and solid state ($^{13}$C—) NMR spectrum. One or more of these techniques may be used to distinguish different polymorphic forms of a compound.

US 2011/251152 describes a number of crystalline forms of Sofosbuvir, i.e. forms 1, 2, 3, 4, 5 and 6, which are characterised by X-ray powder diffraction (XRPD) peaks, as well as an amorphous form. According to this publication, crystalline forms 2, 3, 4 and 5 of Sofosbuvir are said to be prepared by crystallisation from dichloromethane, chloroform, acetonitrile and anisole. However, following filtration and/or drying, these crystalline forms convert to Form 1.

CN 104130302 describes crystalline sofosbuvir form A characterised by XRD Form A is described as a non-solvated, non-hydrated form. The Form A is prepared by dissolving Sofosbuvir in a solvent and adding an antisolvent and allowing the mixture to stand in a sealed vessel for 15-24 hours under certain conditions. The solvent/antisolvent combinations include anhydrous ethanol and one of isopropyl ether, cyclohexane, n-pentane, or toluene or the solvent/anti-solvent may be acetone/n-pentane, acetone/petroleum ether or ethyl acetate/petroleum ether.

Different salts and solid state forms (including solvated forms) of an active pharmaceutical ingredient may possess different properties. Such variations in the properties of different salts and solid state forms and solvates may provide a basis for improving formulation, for example, by facilitating better processing or handling characteristics, changing the dissolution profile in a favorable direction, or improving stability (polymorph as well as chemical stability) and shelf-life. These variations in the properties of different salts and solid state forms may also offer improvements to the final dosage form, for instance, if they serve to improve bioavailability. Different salts and solid state forms and solvates of an active pharmaceutical ingredient may also give rise to a variety of polymorphs or crystalline forms, which may in turn provide additional opportunities to assess variations in the properties and characteristics of a solid active pharmaceutical ingredient.

Discovering new solid state forms and solvates of a pharmaceutical product may yield materials having desirable processing properties, such as ease of handling, ease of processing, storage stability, and ease of purification or as desirable intermediate crystal forms that facilitate conversion to other polymorphic forms. New solid state forms of a pharmaceutically useful compound can also provide an opportunity to improve the performance characteristics of a pharmaceutical product. It enlarges the repertoire of materials that a formulation scientist has available for formulation optimization, for example by providing a product with different properties, e.g., a different crystal habit, higher crystallinity or polymorphic stability which may offer better processing or handling characteristics, improved dissolution profile, or improved shelf-life (chemical/physical stability). For example it has now been found that Form 6 of Sofosbuvir has a high propensity to become electrostatically charged. Electrostatically charged active pharmaceutical ingredients may display poor flowability and/or a tendency to sticking, and thus ultimately may result in difficulties during the operations of the manufacturing process of a pharmaceutical composition based on such an electrostatically charged active pharmaceutical ingredient. Moreover poor content uniformity may be observed in the final dosage form when a dry process such as, for example, dry compression is used to make a pharmaceutical composition with an electrostatically charged active pharmaceutical ingredient. For at least these reasons, there is a need for additional solid state forms (including solvated forms) of Sofosbuvir.

Additionally, the prior art processes for producing crystalline forms of Sofosbuvir, such as those described above, are generally impractical for medium to large scale preparation. Moreover, the resulting products may suffer from polymorphic transformations, which can lead to polymorphically impure materials. Therefore, there is a need in the art to provide further processes for preparing solid state forms of Sofosbuvir.

The present invention aims to provide a new crystalline form of Sofosbuvir, as well as new processes for preparing crystalline forms of Sofosbuvir. In particular, the processes of the present invention enable the production of Form 7 of Sofosbuvir, which may be substantially free of other solid state forms of Sofosbuvir. The processes described herein enable the consistent production of these forms of Sofosbuvir which can be used on a large scale. The present processes also seeks to avoid the need to use a number of different organic solvents, which may cause undesirable and unpredictable polymorphic transformations, and which may lead to the production of mixtures of different crystalline forms, and moreover may introduce undesirable impurities into the product.

SUMMARY OF THE INVENTION

The present invention provides solid state forms of Sofosbuvir, processes for their preparation, and pharmaceutical compositions thereof.

The present invention also encompasses the use of the Sofosbuvir solid state forms of the present invention for the preparation of pharmaceutical compositions of Sofosbuvir.

The present invention comprises processes for preparing the above mentioned pharmaceutical compositions. The processes comprise combining the Sofosbuvir solid state form with at least one pharmaceutically acceptable excipient.

The solid state forms and the pharmaceutical compositions of Sofosbuvir of the present invention can be used as medicaments, particularly for the treatment of Hepatitis C.

The present invention also provides methods of treating Hepatitis C, comprising administering a therapeutically effective amount of the Sofosbuvir solid state form of the present invention, or at least one of the above pharmaceutical compositions, to a subject suffering from Hepatitis C, or otherwise in need of the treatment.

BRIEF DESCRIPTION OF THE DRAWINGS

FIG. 9 gives the X-ray powder diffractogram peaks of Form 7 of Sofosbuvir.

FIG. 11 shows the X-ray powder diffraction peaks for Form 7 sofosbuvir (Example 1) and the relative intensities measured using copper Kα1/Kα2 radiation with a weighted median of the wavelengths of 1.54187 Å. In this table, 2-theta values are reported with an accuracy of ±0.2 degrees 2-theta.

FIG. 12 shows the X-ray powder diffraction peaks for Form 1 sofosbuvir and the relative intensities. In this table, 2-theta values are reported with an accuracy of ±0.2 degrees 2-theta.

DETAILED DESCRIPTION OF THE INVENTION

Figure 1:
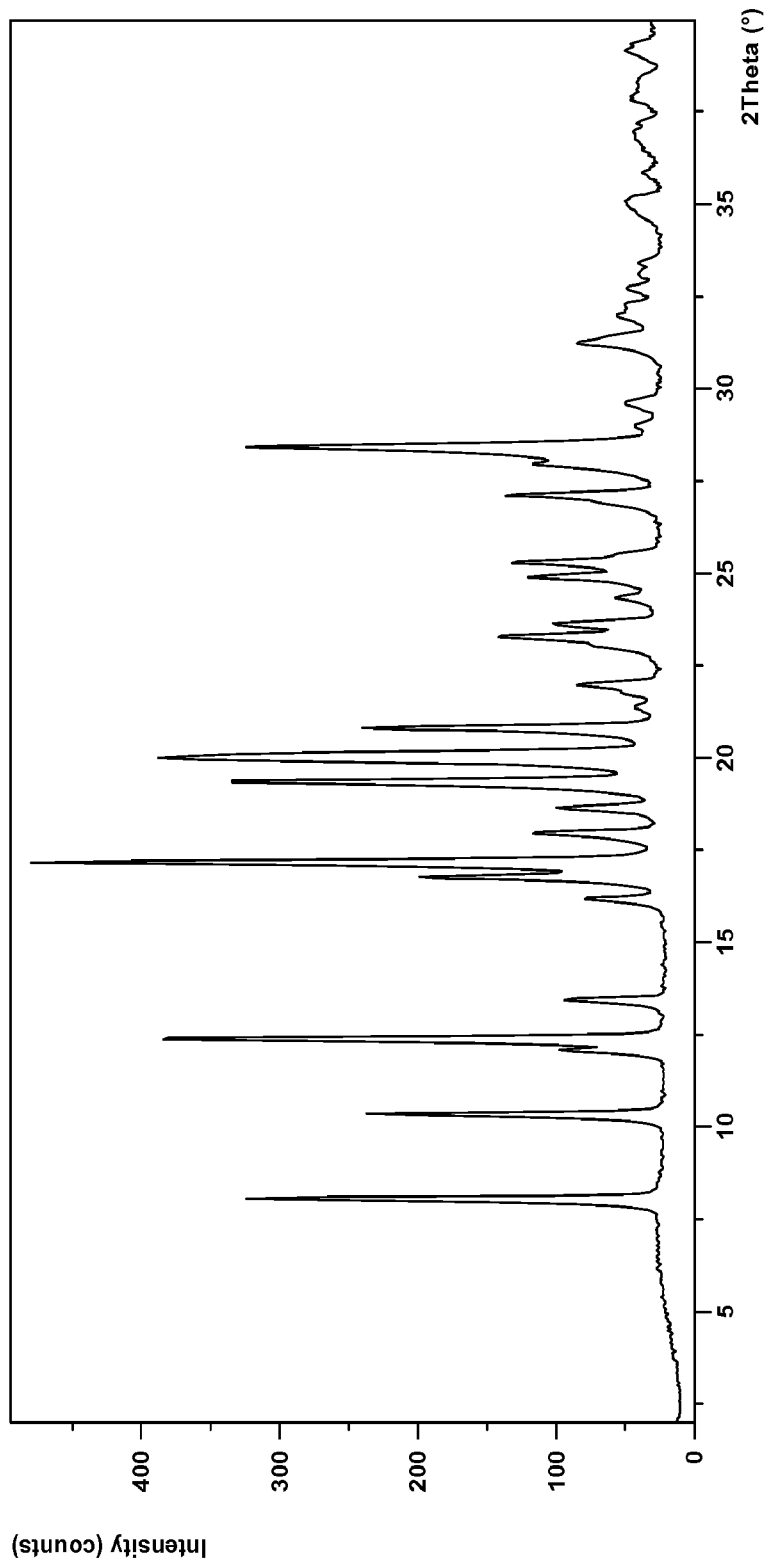
FIG. 1 shows an X-ray powder diffractogram of Form E of Sofosbuvir.

The present invention encompasses solid state forms of Sofosbuvir. Solid state properties of Sofosbuvir can be influenced by controlling the conditions under which the Sofosbuvir is obtained in solid form.

In some embodiments, the solid state/crystalline form of Sofosbuvir of the invention is substantially free of any other forms of Sofosbuvir, or of specified polymorphic forms of Sofosbuvir, respectively.

As used herein, "substantially free" is meant that the solid state forms of the present invention contain 20% (w/w) or less, 10% or less, 5% or less, 2% or less, or 1% or less of any other forms of the subject compound, or of a specified polymorph of Sofosbuvir as measured, for example, by PXRD. According to some embodiments, the salts and solid state forms of the present invention contain 10% (w/w) or less, 5% (w/w) or less, 2% (w/w) or less, 1% (w/w) or less, 0.5% (w/w) or less, or 0.2% (w/w) or less of polymorphs, or of a specified polymorph of Sofosbuvir. In other embodiments, solid state form of Sofosbuvir of the present invention contain from 1% to 20% (w/w), from 5% to 20% (w/w), or from 5% to 10% (w/w) of any solid state forms or of a specified polymorph of Sofosbuvir.

Depending on which other solid state forms comparison is made with, the solid state/crystalline form of Sofosbuvir of the present invention has advantageous properties selected from at least one of the following: chemical purity, flowability, solubility, dissolution rate, morphology or crystal habit, stability—such as chemical stability as well as thermal and mechanical stability with respect to polymorphic conversion, stability towards hydration and/or storage stability, low content of residual solvent, a lower degree of hygroscopicity, flowability, and advantageous processing and handling characteristics such as compressibility, and bulk density.

A solid state form, such as a crystal form or amorphous form, may be referred to herein as being characterized by graphical data "as depicted in" or "as substantially depicted in" a Figure. Such data include, for example, powder X-ray diffractograms. As is well-known in the art, the graphical data potentially provides additional technical information to further define the respective solid state form (a so-called "fingerprint") which cannot necessarily be described by reference to numerical values or peak positions alone. In any event, the skilled person will understand that such graphical representations of data may be subject to small variations, e.g., in peak relative intensities and peak positions due to certain factors such as, but not limited to, variations in instrument response and variations in sample concentration and purity, which are well known to the skilled person. Nonetheless, the skilled person would readily be capable of comparing the graphical data in the Figures herein with graphical data generated for an unknown solid state/crystal form and confirm whether the two sets of graphical data are characterizing the same solid state/crystal form or two different solid state/crystal forms. A solid state/crystal form of a Sofosbuvir referred to herein as being characterized by graphical data "as depicted in" or "as substantially depicted in" a Figure will thus be understood to include any solid state/crystal forms of Sofosbuvir characterized with the graphical data having such small variations, as are well known to the skilled person, in comparison with the Figure.

As used herein, and unless stated otherwise, the term "anhydrous" in relation to solid state/crystalline forms of Sofosbuvir, relates to a solid state/crystalline form of Sofosbuvir which does not include any water (or other solvents) in a defined, stoichiometric amount within the crystal. Moreover, an "anhydrous" form would typically not contain more than 1% (w/w) of either water or organic solvents as measured for example by TGA.

As used herein, the term "isolated" in reference to solid state forms of Sofosbuvir of the present invention corresponds to a solid state form of Sofosbuvir that is physically separated from the reaction mixture in which it is formed.

As used herein, unless stated otherwise, the XRPD measurements are taken using copper $K\alpha$ radiation wavelength 1.5418 Å. Unless otherwise indicated, XRPD 2-theta values are reported with an error of ±0.2 degrees 2-theta.

The individual particles of a sample or aliquot of the solid particulate comprising crystalline form E of Sofosbuvir of the present invention are not of uniform size. Rather, a sample or aliquot of a solid particulate comprising crystalline form E of Sofosbuvir of the present invention is comprised of particles of different sizes that can be size-classified or distributed in an array of discrete, adjacent intervals of particle size. If the size of the intervals is small enough, the array of particle sized approaches a continuum of particle sizes. This collection of discrete particle size intervals together with their population is referred to as the particle size distribution (PSD).

Measurement and characterization of particle size distributions is known in the art. It is possible to compare samples of particulate comprising crystalline form E of Sofosbuvir on the basis of individual points on a cumulative particle size distribution curve. The measurements are represented as d(0.X)=Y (where X and Y are Arabic numerals), each "d" describing an individual point on a cumulative PSD curve. The number "X" represents the percentage (number, volume, or weight) of particles in the population having a nominal size up to and including "Y". Thus, d(0.9)=250μ is characteristic of a PSD in which 90% (number, volume, or weight) of the particles in a population have a nominal size of about 250μ or less (at least some particles having a nominal dimension of 250μ) and so forth. When PSD is determined by the well-known laser-diffraction method described herein, the d(0.X) measurement depicts a volume average.

The skilled artisan knows that the results of PSD determination by one technique can be correlated with results from another technique on an empirical basis by routine experimentation.

As used herein, unless otherwise indicated, "median particle size" refers to the $D_{50}$ value of the particle size distribution. As used herein, particle size distribution is determined by means of laser diffractometry. More specifically, unless otherwise indicated, the particle size was determined using a Mastersizer 2000 from Malvern Instruments—the particle size determination may be carried out as a wet or dry measurement depending on the sample.

The median particle size ($D_{50}$), which is also denoted $D_{50}$-value of the integral volume distribution, is defined in the context of this invention as the particle diameter, at which 50 percent by volume of the particles have a smaller diameter than the diameter which corresponds to the $D_{50}$-value. Likewise, 50 percent by volume of the particles have a larger diameter than the $D_{50}$-value. Analogously, the $D_{90}$-value of the integral volume distribution is defined as the particle diameter, at which 90 percent by volume of the particles have a smaller diameter than the diameter, which corresponds to the $D_{90}$-value. Correspondingly, the $D_{10}$-value of the integral volume distribution is defined as the particle diameter, at which 10 percent by volume of the particles have a smaller diameter than the diameter, which corresponds to the $D_{10}$-value.

According to the invention, "particle diameter" or "particle size" of a particle to be determined means the diameter of an equivalent particle which is assumed to be spherical and to have the same light scattering pattern as the particle to be determined.

A thing, e.g., a reaction mixture, may be characterized herein as being at, or allowed to come to "room temperature" or "ambient temperature", often abbreviated as "RT." This means that the temperature of the thing is close to, or the same as, that of the space, e.g., the room or fume hood, in which the thing is located. Typically, room temperature is from about 20° C. to about 30° C., or about 22° C. to about 27° C., or about 25° C.

The amount of solvent employed in a chemical process, e.g., a reaction or a crystallization, may be referred to herein as a number of "volumes" or "vol" or "V." For example, a material may be referred to as being suspended in 10 volumes (or 10 vol or 10V) of a solvent. In this context, this expression would be understood to mean milliliters of the solvent per gram of the material being suspended, such that suspending a 5 grams of a material in 10 volumes of a solvent means that the solvent is used in an amount of 10 milliliters of the solvent per gram of the material that is being suspended or, in this example, 50 mL of the solvent. In another context, the term "v/v" may be used to indicate the number of volumes of a solvent that are added to a liquid mixture based on the volume of that mixture. For example, adding solvent X (1.5 v/v) to a 100 ml reaction mixture would indicate that 150 mL of solvent X was added.

A process or step may be referred to herein as being carried out "overnight." This refers to a time interval, e.g., for the process or step, that spans the time during the night, when that process or step may not be actively observed. This time interval is from about 8 to about 20 hours, or about 10-18 hours, typically about 16 hours.

As used herein, the term "reduced pressure" refers to a pressure that is less than atmospheric pressure. For example, reduced pressure is about 10 mbar to about 50 mbar.

As used herein, unless indicated otherwise, the term "under vacuum" refers to a pressure of about 0.2 mbar to about 10 mbar, about 0.2 to about 5 mbar, about 0.5 to about 4 mbar, about 1 mbar to about 3 mbar, and preferably about 2 mbar.

As used herein, an "anti-solvent" is a liquid that when combined with a composition comprising a solvent and sofosbuvir, induces precipitation of crystalline Sofosbuvir As used herein, and unless indicated otherwise, the term "compressibility" is expressed as maximum density at constant pressure of 0.2 MPa.

Figure 2:
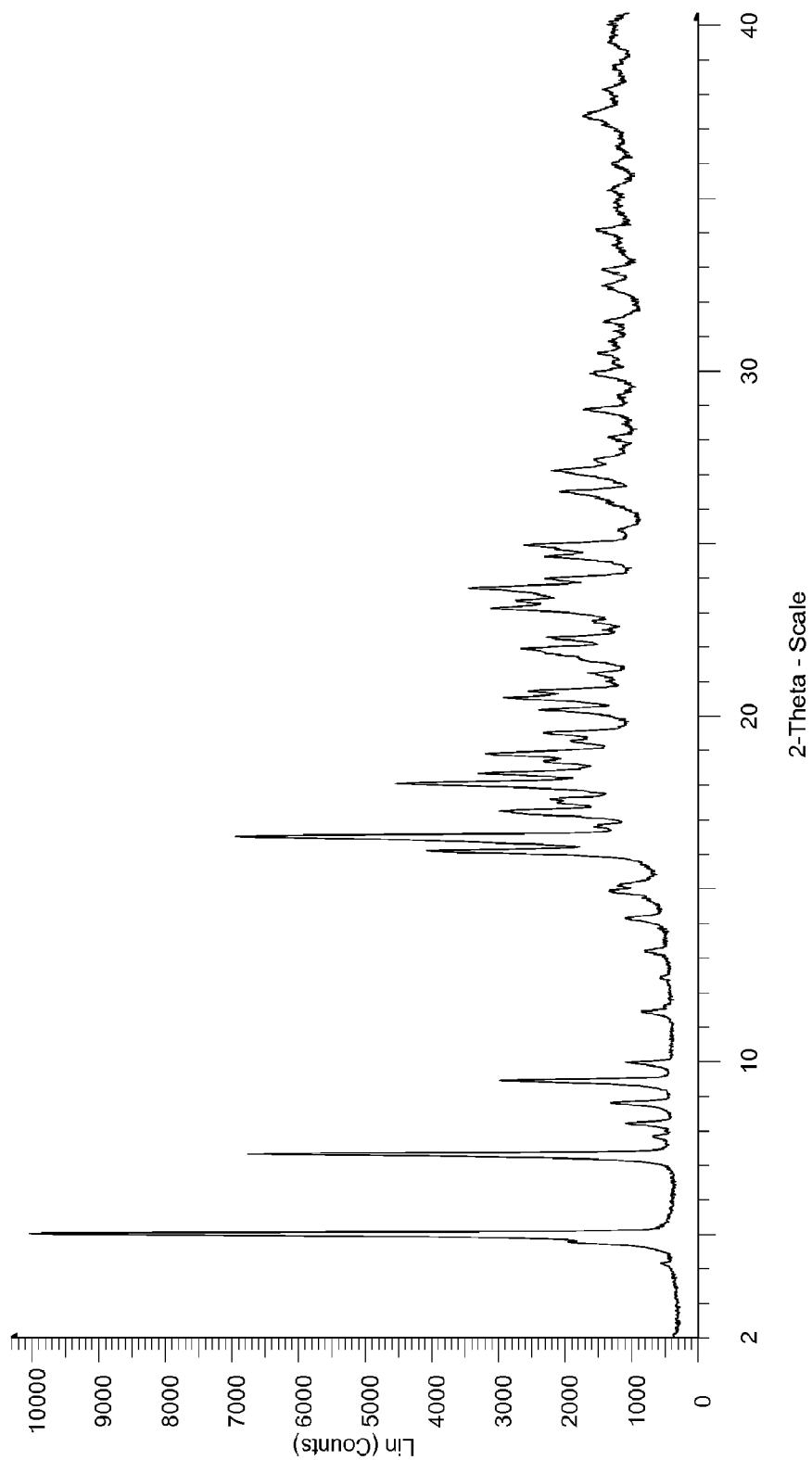
FIG. 2 shows an X-ray powder diffractogram of form 1 of Sofosbuvir.
Figure 3:
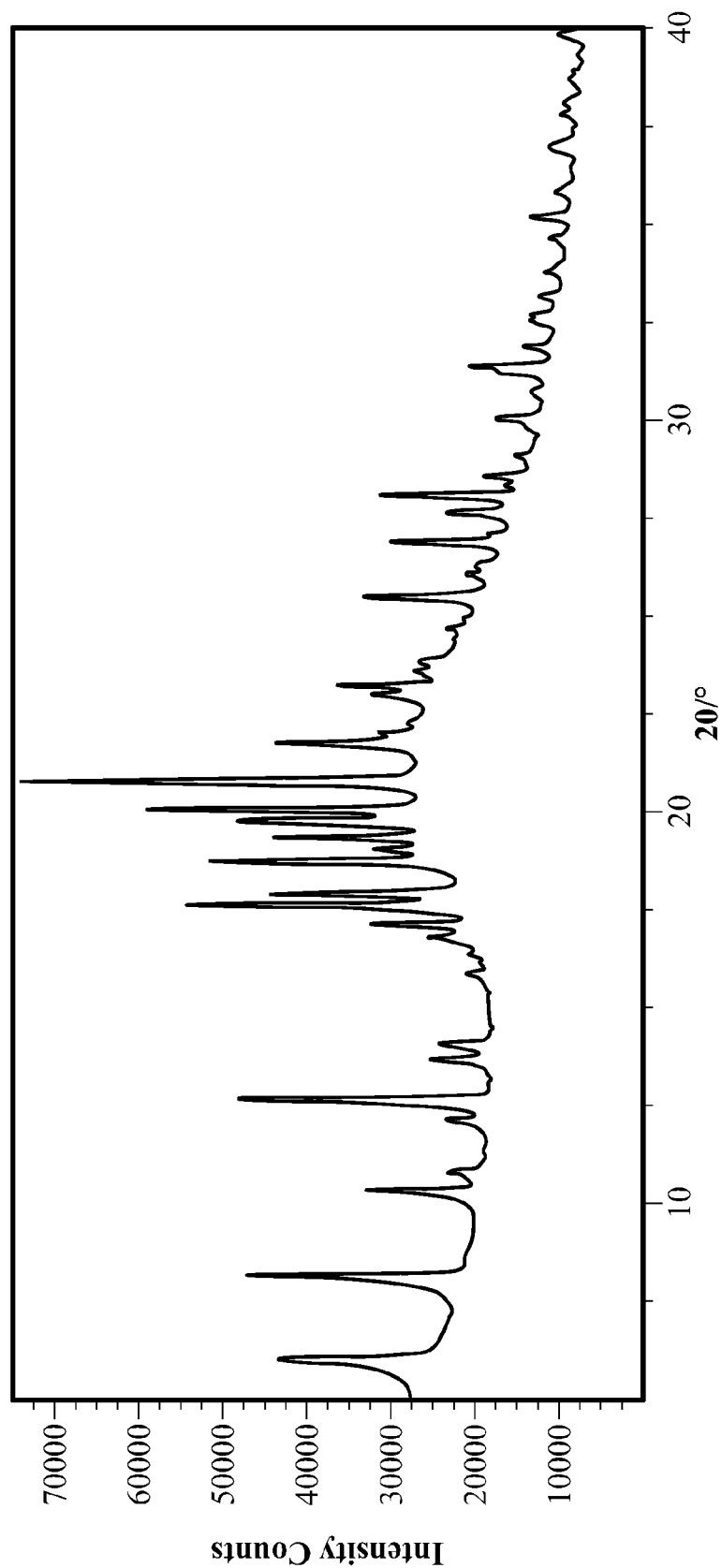
FIG. 3 shows an X-ray powder diffractogram of form 6 of Sofosbuvir

As used herein crystalline form 1 of Sofosbuvir refers to a crystalline form which may be characterized by X-ray powder diffraction pattern as depicted in FIG. 2. Crystalline form 1 of Sofosbuvir may be characterized by XRPD peaks or the X-ray powder diffractogram disclosed in US 2011/0251152 or WO2011/123645. As used herein crystalline form 6 of Sofosbuvir refers to a crystalline form as described in US 2011/0251152, which may be characterized by X-ray powder diffraction pattern as depicted in FIG. 3. Thus, crystalline Form 6 of Sofosbuvir may be characterised by an X-ray powder diffraction pattern having peaks as disclosed in US 2011/0251152 or WO2011/123645, which is depicted in FIG. 3.

In one embodiment, the present invention comprises crystalline form of Sofusbovir, designated Form 7, characterized by data selected from one or more of the following: X-ray powder diffraction pattern having peaks at 12.4, 13.5, 16.2, 25.3, and 27.2 degrees two theta; an X-ray powder diffraction pattern as depicted in FIG. 8; and combinations of these data.

Crystalline Form 7 of Sofosbuvir may be further characterized by the X-ray powder diffraction pattern having peaks at 8.1, 10.4, 17.2, 19.4, and 20.9 degrees two theta.

Figure 8:
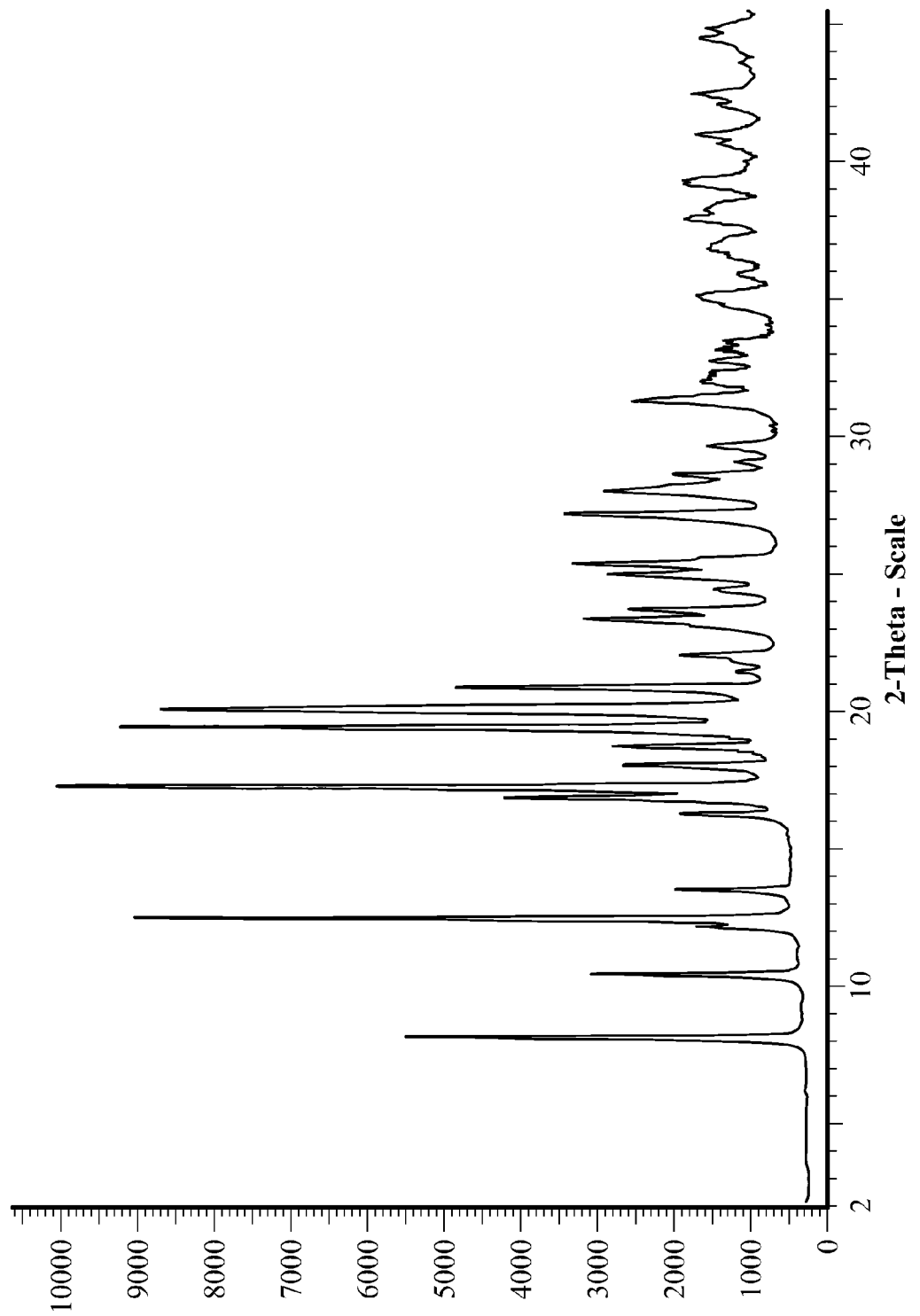
FIG. 8 shows an X-ray powder diffractogram of Form 7 of Sofosbuvir

Crystalline Form 7 of Sofosbuvir may be characterized by each of the above characteristics alone and/or by all possible combinations, e.g. by X-ray powder diffraction pattern having peaks at 12.4, 13.5, 16.2, 25.3, and 27.2 degrees two theta±0.2 degrees two theta and by an X-ray powder diffraction pattern as depicted in FIG. 8. Crystalline Form 7 of Sofosbuvir may also be characterised by an X-ray diffraction pattern having the peaks listed in the table in FIG. 9.

Figure 10:
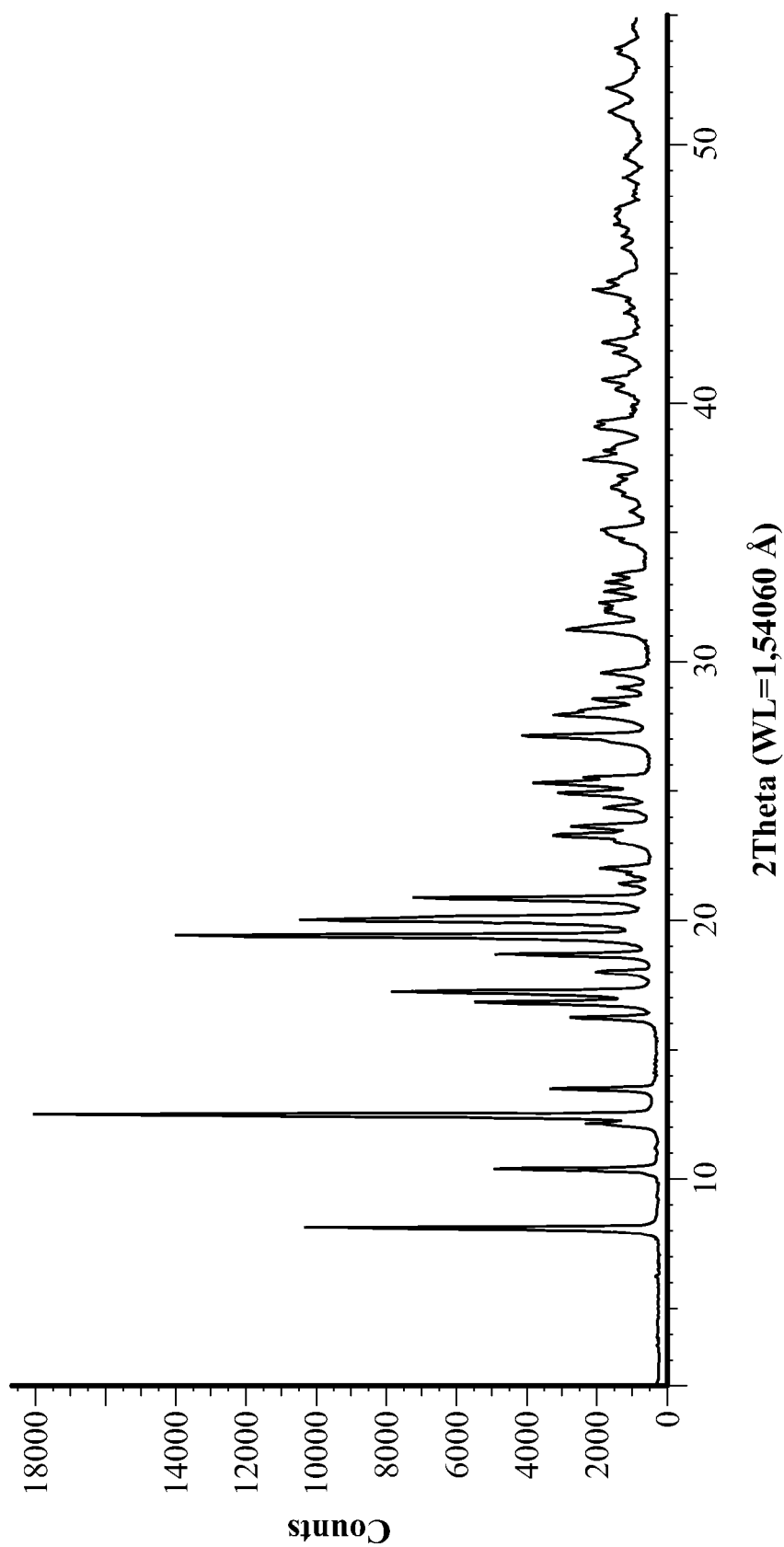
FIG. 10 shows an X-ray powder diffractogram of Form 7 of Sofosbuvir (Example 1) measured using copper Kα1/Kα2 radiation with a weighted median of the wavelengths of 1.54187 Å.

Alternatively, Form 7 may be further characterised by the XRPD peak listing in the first column of the table in FIG. 11, and optionally may be characterised by the XRPD peak listings in Table 11 including the intensities, and/or an X-ray powder diffractogram substantially as depicted in FIG. 10.

In one embodiment of the present invention, Form 7 of Sofosbuvir is isolated.

The present invention further encompasses 1) a pharmaceutical composition comprising Form 7 of Sofosbuvir as described herein; 2) a pharmaceutical formulation comprising Form 7 of Sofosbuvir or pharmaceutical compositions described herein, and at least one pharmaceutically acceptable excipient; 3) a process to prepare such formulations comprising combining Form 7 of Sofosbuvir described herein and at least one pharmaceutically acceptable excipient; 4) the use of Form 7 of Sofosbuvir described herein in the manufacture of a pharmaceutical composition, and 5) a method of treating a subject suffering from Hepatitis C, or otherwise in need of the treatment comprising administering a therapeutically effective amount of Form 7 of Sofosbuvir described herein, optionally in the form of pharmaceutical compositions or formulations. Typically, the pharmaceutical composition is a solid composition and the Sofosbuvir retains its solid state form. The pharmaceutical compositions can be prepared by a process comprising combining Form 7 of Sofosbuvir with at least one pharmaceutically acceptable excipient. Form 7 of Sofosbuvir of the present invention can also be used as a medicament.

In a first aspect, the present invention provides a process for preparing Sofosbuvir crystalline form 7 comprising: (a) contacting sofosbuvir with a solvent system comprising water and optionally an organic solvent, (b) allowing the mixture to stand for a period of time sufficient to form Sofosbuvir crystalline form 7. Optionally the Sofosbuvir crystalline form 7 may be isolated from the reaction mixture, and may be dried.

The solvent system employed in the process of the present invention comprises water and optionally an organic solvent. Preferably the water is deionized water. It is preferred that the solvent system comprises water and an organic solvent. The organic solvent is preferably not freely miscible with water. Thus, water is preferably soluble in certain concentrations in the organic solvent to form a single phase, but is not soluble in all concentrations. Preferably, the organic solvent has a water miscibility at room temperature (i.e. 18° C. to about 30° C., about 18° C. to about 28° C., about 18° C. to about 25° C. or about 20° C. to about 25° C.) such that water is soluble in the organic solvent at concentrations of from about 0.1 to about 20% (w/w), about 0.1 to about 10% (w/w), about 0.2 to about 5% (w/w), about 0.5 to about 5% (w/w), about 0.5 to about 5% (w/w) or about 1 to about 3% (w/w). More preferably, the organic solvent has a water miscibility such that water is soluble in the organic solvent at concentrations about 0.5 to about 5 wt %, about 0.5 to about 5 wt % or about 1 to about 3 wt %.

Suitable organic solvents include those selected from the group consisting of: aliphatic ethers (preferably $C_{4-8}$ dialkyl ethers), cyclic ethers (preferably $C_{1-3}$ alkyl-substituted $C_{4-8}$ cyclic ethers), ketones (preferably $C_{4-8}$ ketones), alcohols (preferably $C_{4-8}$ aliphatic alcohol) and esters (preferably $C_{1-4}$ alkyl esters of $C_{4-8}$ alcohols). Especially preferred organic solvents are selected from the group consisting of: diethyl ether, dipropyl ether, diisopropylether, dibutyl ether, tert-amyl methyl ether, methyl tert-butyl ether, methyl isopropyl ether, 2-methyltetrahydrofuran, ethyl tert-butyl ether, methyl isobutyl ketone, diethyl ketone, methyl butyl ketone, isoamyl alcohol, ethyl acetate, and n-butyl acetate. Methyl tert-butyl ether is a particularly preferred organic solvent for use in the process of the present invention.

In step (a) of the present process, the solvent system comprising water and an organic solvent may be in the form of a water-saturated organic solvent, wherein the organic solvent is preferably $C_{4-8}$ dialkyl ether or $C_{1-3}$ alkyl-substituted $C_{4-8}$ cyclic ether, and preferably a $C_{4-8}$ dialkyl ether. The water-saturated organic solvent can be a mixture of methyl tert-butyl ether and water. Preferably, the solvent system is water-saturated methyl tert-butyl ether.

Typically, water-saturated methyl tert-butyl ether may contain about 0.5 to about 3 wt %, about 0.8 to about 2 wt % or about 1 to about 1.5 wt % water. Water-saturated methyl tert-butyl ether may be prepared by a process comprising stirring the organic solvent with a sufficient excess of water to form a biphasic mixture, and discarding the aqueous phase. For example, the solvent system may be prepared by a process comprising stirring methyl tert-butyl ether with water in a volume ratio of MTBE:water of from: about 5:1 to about 25:1, about 5:1 to about 20:1, about 5:1 to about 15:1, about 8:1 to about 12:1, or about 10:1, and discarding the aqueous phase.

In the process of the present invention, the amount of solvent system per gram of Sofosbuvir in step (a) is preferably from about 5 ml to about 25 ml, about 5 ml to about 20 ml, about 10 ml to about 20 ml, about 12 ml to about 18 ml, or about 15 to about 16 ml. Preferably, the mixture in step (a) is a solution of Sofosbuvir in the solvent system. The mixture of Sofosbuvir with the solvent system in step (a) may be filtered in order to remove undissolved solid prior to step (b).

Step (b) comprises allowing the mixture of Sofosbuvir and solvent system to stand for a period of time sufficient to form sofosbuvir crystalline form 7. The formation of Sofosbuvir crystalline form 7 may be monitored by X-ray powder diffraction analysis. Preferably, the mixture is allowed to stand at a temperature of from: about 10° C. to about 80° C., about 15° C. to about 60° C., about 15° C. to about 40° C., about 18 to about 30° C., or about 20 to about 25° C.

For the formation of Sofosbuvir form 7, the mixture in step (b) may be seeded with crystalline Sofosbuvir form 7. Preferably, for the formation of Sofosbuvir form 7, after optional seeding, the mixture is allowed to stand for about 12 to about 96 hours, about 18 to about 60 hours, or about 30-50 hours.

In a preferred embodiment of the present invention, for the formation of Sofosbuvir form 7, the mixture of Sofosbuvir with the solvent system is allowed to stand without stirring, preferably in a closed vessel. If it is said that a mixture is stored overnight this means that the mixture is allowed to stand without stirring overnight.

The process of the present invention may be used to prepare Form 7 of Sofosbuvir, which may be characterised by an X-ray powder diffraction pattern having one or more peaks at about: 12.4, 13.5, 16.2, 25.3, and 27.2±0.2 degrees two theta. Preferably, the crystalline Form 7 Sofosbuvir may be characterised by an X-ray powder diffraction pattern having two, three, four or five peaks at about: 12.4, 13.5, 16.2, 25.3, and 27.2±0.2 degrees two theta. More preferably, the crystalline Form 7 Sofosbuvir is characterised by an X-ray powder diffraction pattern having peaks at about: 12.4, 13.5, 16.2, 25.3, and 27.2±0.2 degrees two theta. Additionally, crystalline Form 7 of Sofosbuvir may be further characterised by having X-ray powder diffraction pattern with one or more peaks at about: 8.1, 10.4, 17.2, 19.4, and 20.9±0.2 degrees two theta, preferably further having characteristic X-ray powder diffraction pattern with two, three, four or five peaks at about: 8.1, 10.4, 17.2, 19.4, and 20.9±0.2 degrees two theta and more preferably further having characteristic X-ray powder diffraction pattern with peaks at about: 8.1, 10.4, 17.2, 19.4, and 20.9±0.2 degrees two theta.

In a preferred embodiment of the present invention, the crystalline Form 7 of Sofosbuvir prepared by the process of the present invention is characterised by an X-ray powder diffraction pattern having peaks at about: 8.1, 10.4, 12.4, 13.5, 16.2, 17.2, 19.4, 20.9, 25.3, and 27.2±0.2 degrees two theta. The crystalline form 7 of Sofosbuvir prepared by the process of the present invention may alternatively be characterised by XRPD peak 2-theta values as listed in FIG. 11 optionally with the corresponding intensity values. Alternatively the crystalline Form 7 of Sofosbuvir prepared by the process of the present invention may be characterised by an X-ray powder diffraction pattern substantially as depicted in FIG. 10. Crystalline Form 7 Sofosbuvir prepared by the process of the present invention may be alternatively or additionally characterised by having lattice parameters at 120K substantially as follows:

| | |
|---|---|
| Cell length a: | 5.17 Å |
| Cell length b: | 16.85 Å |
| Cell length c: | 14.44 Å |
| Cell angle alpha: | 90° |
| Cell angle beta: | 100.2° |
| Cell angle gamma: | 90° |

The crystalline Form 7 Sofosbuvir prepared according to the process of the present invention is advantageously in the form of rod-shaped crystals. Moreover, the crystalline form 7 sofosbuvir prepared according to the process of the present invention has an advantageous particle size distribution. Particularly, crystalline Form 7 Sofosbuvir prepared according to the process of the present invention has a particle size distribution $D_{10} \geq 4$ µm, preferably 4-10 µm, as measured by laser diffractometry.

Preferably, crystalline Form 7 Sofosbuvir prepared according to the process of the present invention has a $D_{50}$ particle size distribution selected from: ≥about 25 µm, about 15 to about 300 µm, about 20 to about 250 µm, about 20 to about 200 µm, about 20 to about 150 µm, about 20 to about 75 µm, or about 25 to about 50 µm, as measured by laser diffractometry. More preferably, crystalline Form 7 Sofosbuvir prepared according to the process of the present invention has a $D_{90}$ particle size distribution selected from ≥about 75 µm, about 50 to about 500 µm, about 60 to about 400 µm, about 75 to about 300 µm, about 75 to about 200 µm, or about 75 to about 150 µm, as measured by laser diffractometry.

Moreover, the process of the present invention advantageously enables the consistent production of Form 7 Sofosbuvir which is substantially free of any other crystalline form of Sofosbuvir—for example, the Form 7 Sofosbuvir is typically free of crystalline Form 1 and Form 6 of sofosbuvir, as measured by XRPD.

In any aspect of the present invention, the sofosbuvir starting material in step (a) can be any solid state form of sofosbuvir. Preferably the sofosbuvir starting material in step (a) is crystalline Form 1 as described above.

Following isolation of the sofosbuvir form 7, the product may be dried under vacuum. For example, the drying may be carried out at a temperature of about 18° C. to about 30° C., about 20° C. to about 25° C., or at room temperature.

The present invention further encompasses Sofosbuvir crystalline form 7 prepared by any embodiment of the process as set out herein. Moreover, the process of the present invention may further comprise combining the sofosbuvir crystalline form 7 with one or more pharmaceutically acceptable excipients to form a pharmaceutical composition thereof. The present invention further comprises a pharmaceutical composition comprising Sofosbuvir crystalline form 7 prepared by any embodiment of the process as set out herein.

The crystalline forms of Sofosbuvir prepared by a process according to any embodiment of the present invention may be substantially free of any other forms of Sofosbuvir, or of specified polymorphic forms of Sofosbuvir, respectively.

Depending on which other solid state forms comparison is made with, Form 7 of Sofosbuvir such as prepared according to any embodiment of the present invention, has advantageous properties selected from at least one of the following: chemical purity, flowability, solubility, dissolution rate, morphology or crystal habit, stability, such as chemical stability as well as thermal and mechanical stability with respect to polymorphic conversion and/or storage stability, low content of residual solvent, a lower degree of hygroscopicity, flowability, and advantageous processing and handling characteristics such as compressibility, and bulk density. Particularly, the Form 7 Sofosbuvir is stable to polymorphic conversion. Moreover, Form 7 of Sofosbuvir may have advantageous crystal habit and/or particle size distribution. For example, the Form 7 Sofosbuvir can be readily isolated from the reaction mixture by filtration, and/or may have a low propensity to stick to tableting machinery. Such properties are advantageous as it enables the crystalline form to be easily processed into pharmaceutical formulations.

The form 7 of sofosbuvir prepared according to the process of the present invention has an improved solubility. Preferably form 7 of sofosbuvir has a solubility of ≥65% at pH 6.8 after 5 minutes such as between 65% to 80% after 5 minutes.

The form 7 of sofosbuvir prepared according to the process of the present invention has an improved dissolution, especially when compared to form 6. Preferably form 7 of sofosbuvir has a dissolution of ≥3 mg/ml in water after 15 min at 37° C., such as between 3 mg/ml and 4 mg/ml in water after 15 min at 37° C.

In any embodiment of the present invention, the crystalline Form 7 of Sofosbuvir including the Form 7 produced by the processes described herein, is substantially free of crystalline Form 6 Sofosbuvir. Particularly, the crystalline form of Sofosbuvir of the present invention contains: less than 10 wt %, less than 5 wt %, less than 2 wt %, less than 1 wt %, less than 0.5 wt %, or less than 0.2 wt % of crystalline Form 6 Sofosbuvir.

The present invention further encompasses Sofosbuvir crystalline form 7 prepared by the process as described in any of the embodiments, as well as a pharmaceutical composition comprising Sofosbuvir crystalline form 7 prepared by the process as described in any of the embodiments described herein.

The present invention comprises a process for preparing the above mentioned pharmaceutical compositions. The process comprises combining the Sofosbuvir solid state form with at least one pharmaceutically acceptable excipient.

Figure 7:
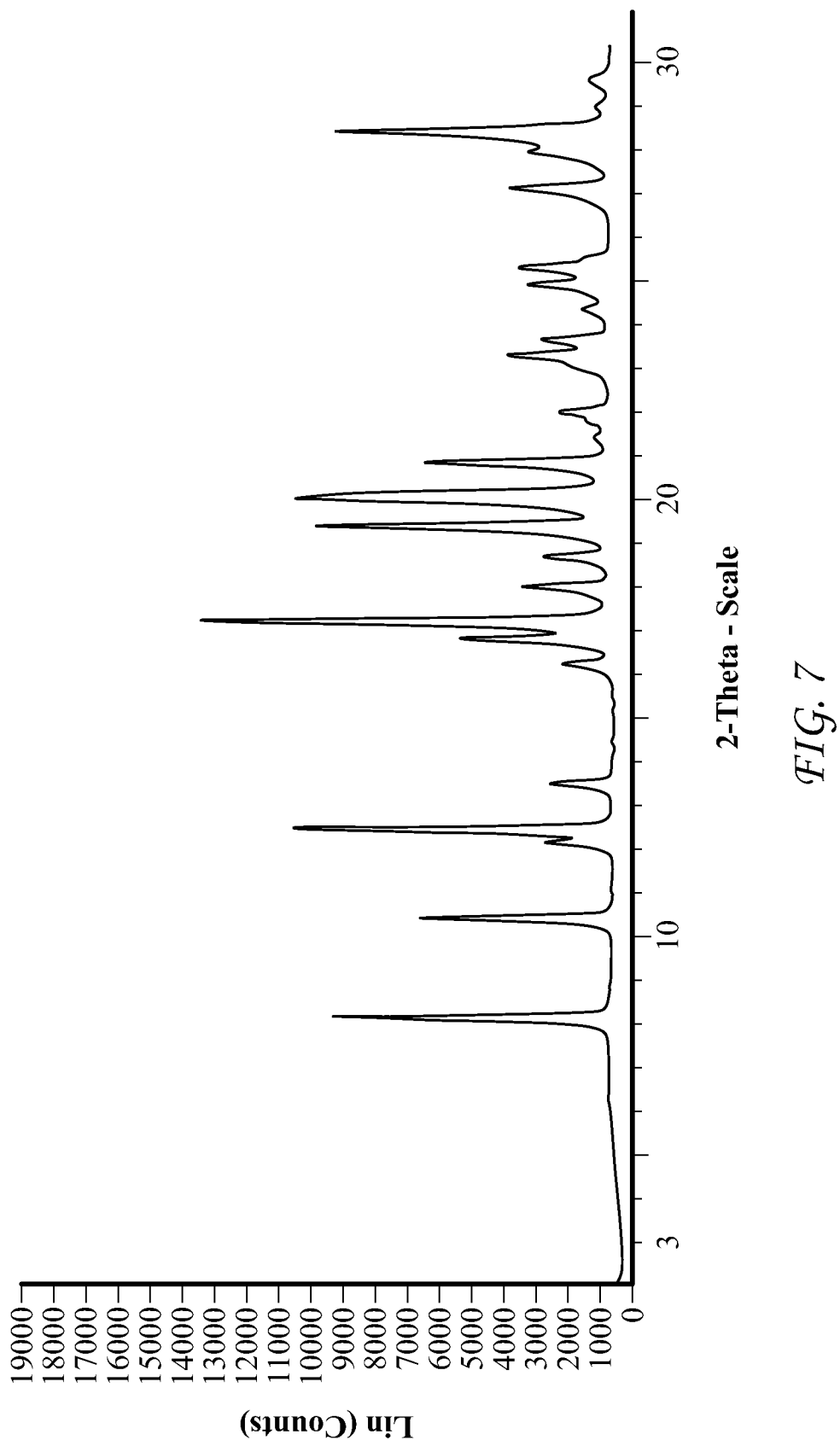
FIG. 7—XRPD of Form E Sofosbuvir in 2-30 degrees 2-theta range

In one embodiment, the present invention comprises a crystalline form of Sofosbuvir, designated form E, characterized by data selected from one or more of the following: an X-ray powder diffraction pattern as depicted in FIG. 1 or FIG. 7; an X-ray powder diffraction pattern having peaks at: 12.4, 16.2, 17.2, 25.0 and 25.3 degrees two theta ±0.1 degrees two theta; an X-ray powder diffraction pattern having peaks at: 12.4, 16.2, 17.2, 25.0 and 25.3 degrees two theta±0.1 degrees two theta and absence of peaks at: 10.9 and 14.2 degrees two theta±0.2 degrees two theta; and combinations of these data.

Crystalline form E of Sofosbuvir may be further characterized by data selected from one or more of the following: X-ray powder diffraction pattern having peaks at 12.4, 16.2, 17.2, 25.0 and 25.3 degrees two theta±0.1 degrees two theta and also having one, two, three or four peaks selected from: 8.1, 19.4, 22.0 and 23.3 degrees two theta±0.1 degrees two theta; an X-ray powder diffraction pattern having peaks at: 12.4, 16.2, 17.2, 25.0 and 25.3 degrees two theta±0.1 degrees two theta, absence of peaks at: 10.9 and 14.2 degrees two theta±0.2 degrees two theta and also having one, two, three or four peaks selected from: 8.1, 19.4, 22.0 and 23.3 degrees two theta±0.1 degrees two theta.

Crystalline form E of Sofosbuvir may be characterized by an X-ray powder diffraction pattern having peaks at 8.1, 12.4, 16.2, 17.2, 19.4, 22.0, 23.3, 25.0 and 25.3 degrees two theta±0.1 degrees two theta. Alternatively, crystalline form E of Sofosbuvir may be characterized by an X-ray powder diffraction pattern having peaks at 8.1, 12.4, 16.2, 17.2, 19.4, 22.0, 23.3, 25.0 and 25.3 degrees two theta±0.1 degrees two theta and an absence of peaks at 10.9 and 14.2 degrees two theta±0.2 degrees two theta.

Crystalline form E of Sofosbuvir may be further characterized by the data set forth in the following table.

TABLE

| X-ray powder diffraction peaks of Form E of Sofosbuvir: Angle (degrees two-theta ± 0.1 degrees two theta. |
| --- |
| 8.1 |
| 10.4 |
| 12.1 |
| 12.4 |
| 13.5 |
| 16.2 |
| 16.8 |
| 17.2 |
| 18.0 |
| 18.7 |
| 19.4 |
| 20.1 |
| 20.9 |
| 22.0 |
| 23.3 |
| 23.7 |
| 24.4 |

In another embodiment crystalline form E may be characterized by X-ray powder diffraction pattern having peaks at: 8.1, 12.1, 12.4, 13.5, 16.2 and 17.2 degrees two-theta±0.1 degrees two theta. In a preferred embodiment, the present invention relates to a pharmaceutical composition comprising form E of sofosbuvir, wherein form E is characterized by X-ray powder diffraction pattern having peaks at: 8.1, 12.1, 12.4, 13.5, 16.2 and 17.2 degrees two-theta±0.1 degrees two theta.

In another embodiment form E may be characterized by X-ray powder diffraction pattern having peaks at: 8.1, 12.1, 12.4, 13.5, 16.2 and 17.2 degrees two-theta±0.2 degrees two theta, and absence of peaks at: 10.9 and 14.2 degrees two theta±0.2 degrees two theta. In a preferred embodiment, the present invention relates to a pharmaceutical composition comprising form E of sofosbuvir wherein Form E is characterised by an X-ray diffraction pattern having peaks at 8.1, 12.1, 12.4, 13.5, 16.2 and 17.2 degrees two theta±0.2 degrees two theta, and absence of peaks at: 10.9 and 14.2 degrees two theta±0.2 degrees two theta.

In another embodiment crystalline form E may be characterized by X-ray powder diffraction pattern having peaks at: 8.1, 10.4, 13.5, 18.0 and 18.7 degrees two-theta±0.1 degrees two theta. In a preferred embodiment, the present invention relates to a pharmaceutical composition comprising form E of sofosbuvir, wherein form E is characterized by X-ray powder diffraction pattern having peaks at: 8.1, 10.4, 13.5, 18.0 and 18.7 degrees two-theta±0.1 degrees two theta.

In another embodiment form E may be characterized by X-ray powder diffraction pattern having peaks at: 8.1, 10.4, 13.5, 18.0 and 18.7 degrees two-theta±0.2 degrees two theta, and absence of peaks at: 10.9 and 14.2 degrees two theta±0.2 degrees two theta. In a preferred embodiment, the present invention relates to a pharmaceutical composition comprising form E of sofosbuvir wherein Form E is characterised by an X-ray diffraction pattern having peaks at 8.1, 10.4, 13.5, 18.0 and 18.7 degrees two theta±0.2 degrees two theta, and absence of peaks at: 10.9 and 14.2 degrees two theta±0.2 degrees two theta.

In another embodiment the present invention is directed to a monoclinic crystalline form of sofosbuvir, space group P2$_1$ having the following unit cell parameters a~14.47 Å, b~17.02 Å, c~5.22 Å, alpha~90.00°, beta~100.30° and gamma~90.00°, preferably as obtained by synchrotron radiation at wavelength 0.40003(1) Å. It can be understood that the above unit cell parameters can be obtained by indexation from high resolution powder pattern obtained in synchrotron radiation at wavelength 0.40003(1) Å.

In one embodiment Form E is anhydrous.

Form E has advantages as discussed above. Particularly, form E is stable for at least 3 months at 40 degrees and at 25 degrees.

In one embodiment of the present invention, crystalline form E of Sofosbuvir is isolated.

Figure 4:
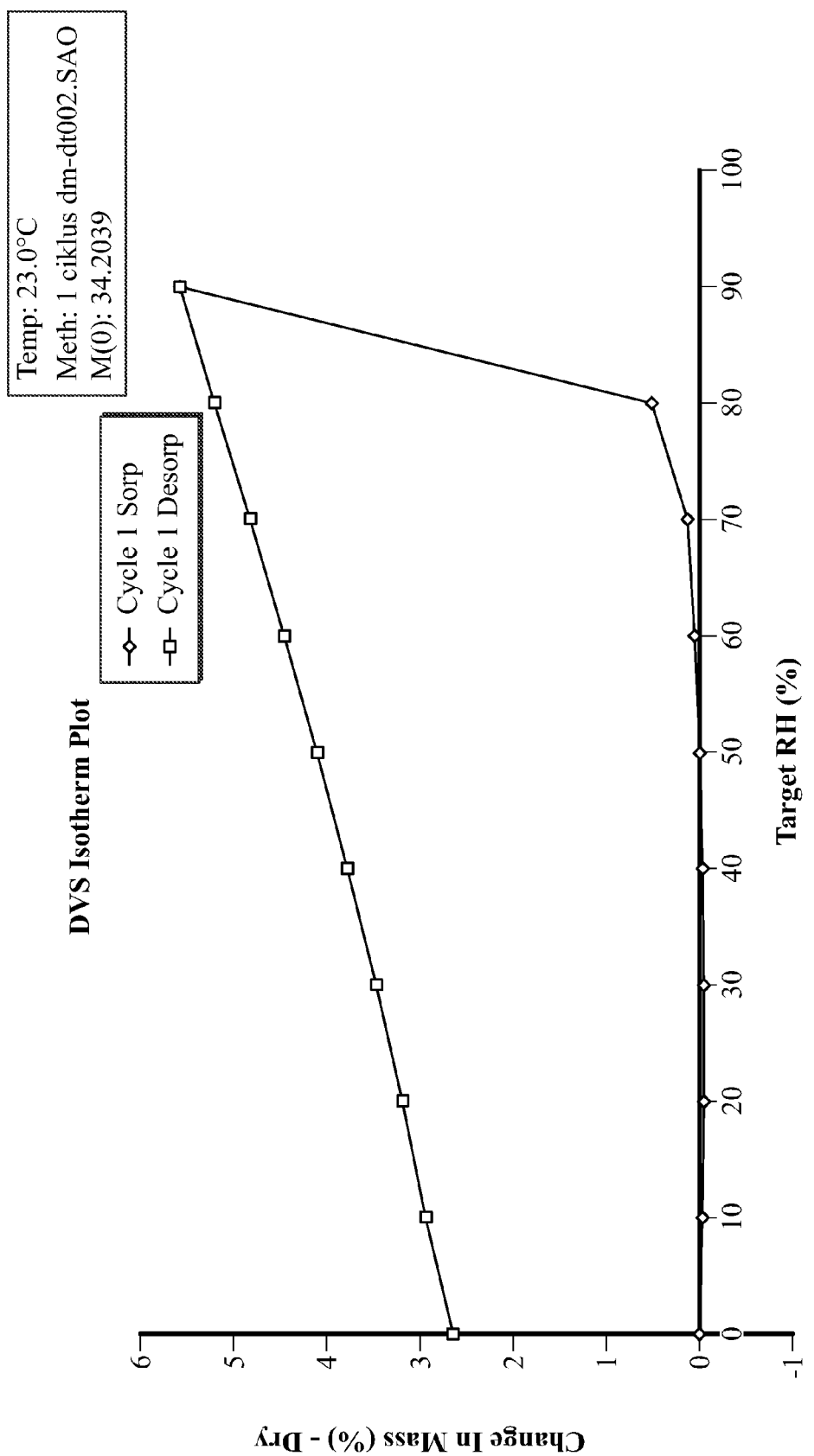
FIG. 4 shows the DVS isotherm Plot of form 1 of Sofosbuvir
Figure 5:
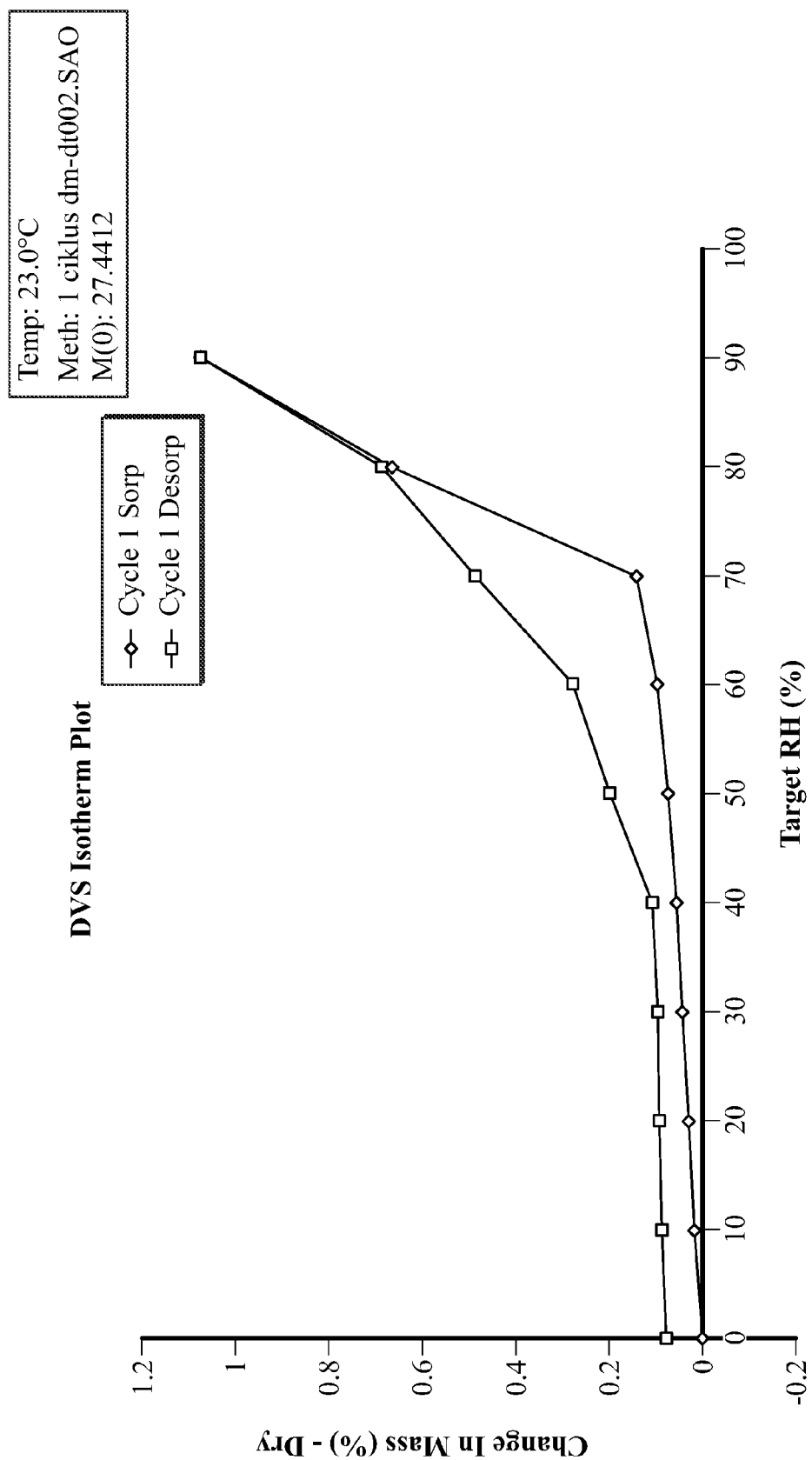
FIG. 5 shows the DVS isotherm of form 6 of Sofosbuvir

Compositions comprising crystalline form E of the present invention are preferably polymorphically pure i.e., it is substantially free of any other forms of sofosbuvir. For example crystalline form E of the present invention is substantially free of form 6 of sofosbuvir. Specifically, crystalline form E of the present invention contains 20% or less, 10% or less, 5% or less, 2% or less, 1% or less, of form 6 of sofosbuvir as measured by PXRD. Accordingly, the content of crystalline Sofosbuvir form 6 in crystalline Sofosbuvir form E will be measured by detecting and quantifying the described characteristic peaks of form 6. The characteristic peaks of crystalline Sofosbuvir form 6 used for the above described measurement can be any one or both peaks at: 6.08 and 10.85 degrees two theta±0.2 degrees two theta. In a preferred aspect, the present invention encompasses solid forms of Sofosbuvir comprising crystalline form E of Sofosbuvir having preferred hygroscopic properties, i.e it is less hygroscopic in comparison to form 1 and form 6 of Sofosbuvir. This property can be evidenced by the DVS data presented in FIGS. 4, 5 and 6 and by the following table:

TABLE 2

| Relative humidity | Change in Mass (%) | | |
|---|---|---|---|
| | Form 1 | Form 6 | Form E |
| 70% | 0.13 | 0.14 | 0.07 |
| 90% | 5.57 | 1.08 | 0.12 |

Solid forms of crystalline form E with low hygroscopicity, according to the present invention, can be easily handled, processed and stored, without need of specially controlled conditions, and may therefore be advantageously used for the preparation of pharmaceutical compositions and formulations.

The improved hygroscopic properties discussed herein above may be expressed by the dynamic water uptake monitored by the DVS instrument. The profile of the dynamic curve obtained may provide insight on the tendency of the substance to deliquescence. This is expressed by an abrupt change in slope of the curve (inflection point) which indicates that at a certain critical relative humidity the substance starts to absorb significant quantities of water. This behavior indicates a long-term possibility of the stored powder to stick and form lumps.

The DVS curve of form 1 of sofosbuvir (depicted in FIG. 4) exhibits a critical relative humidity in the sorption curve at about 80% RH at which the rate of water uptake changes (inflection point). A significant water uptake is observed above 80% RH (about 5%). This indicates that the sample may partially liquefy during long term storage or during exposure to high humidity.

The DVS curve of form 6 (depicted in FIG. 5) of sofosbuvir exhibits a critical relative humidity in the sorption curve at about 70% RH at which the rate of water uptake changes (inflection point). A significant water uptake is observed above 70% RH (about 1%). This indicates that also this sample may partially liquefy during long term storage or during exposure to high humidity.

Surprisingly it was found that Sofosbuvir comprising form E of low hygroscopicity does not show this inflection point. Further, this form E doesn't exhibit any hysteresis between the desorption and the absorption isotherm. The hysteresis between the absorption and desorption is defined as the loop that appears in the figure as a result of gap which forms between the absorption weight increase value and desorption weight decrease value at a given relative humidity. A comparison of the water content values as measured by DVS is shown in Table 2 above.

Figure 6:
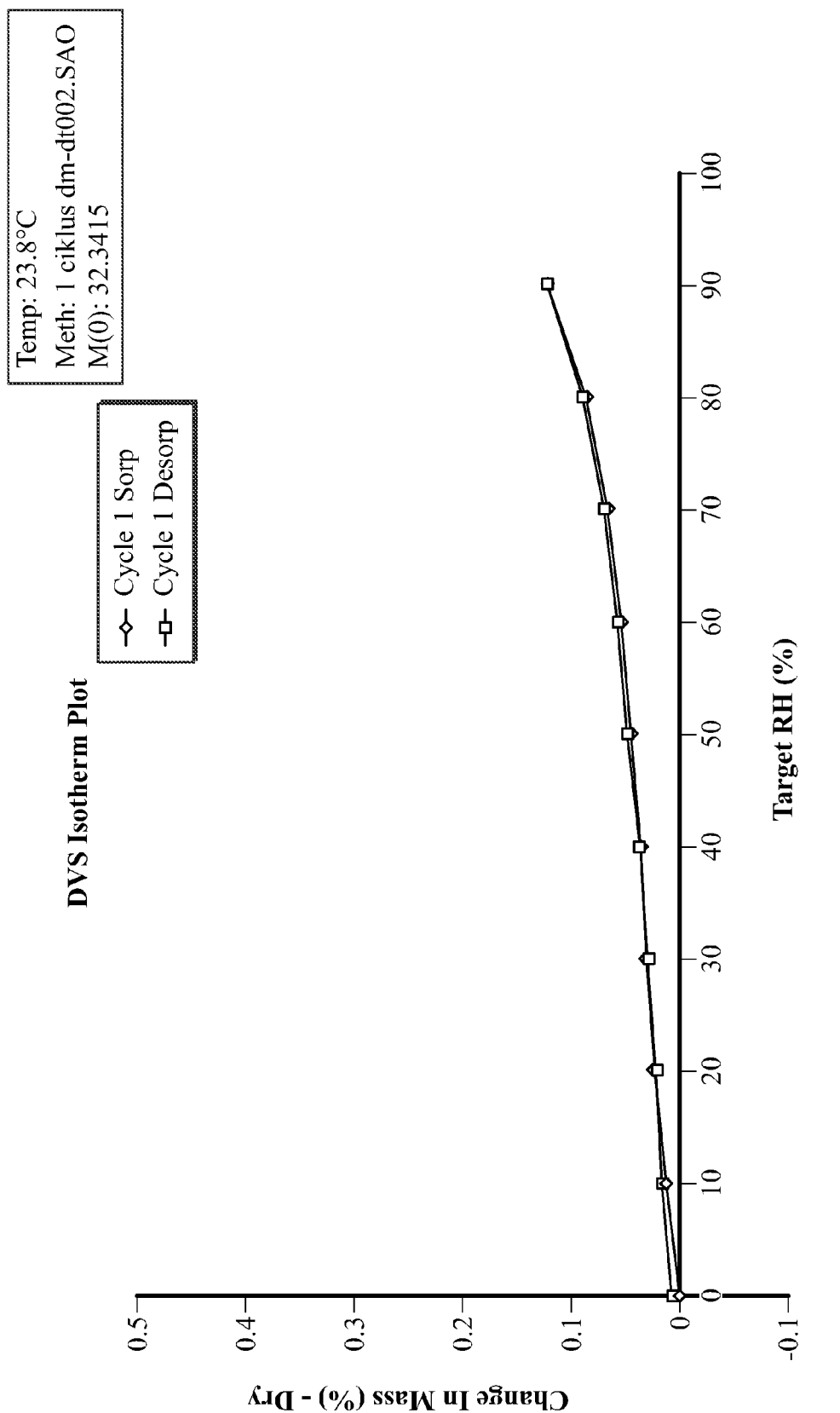
FIG. 6 shows the DVS isotherm of form E of Sofosbuvir, prepared according to example 7

In another aspect the present invention provides a solid form of sofosbuvir, preferably a crystalline form of sofosbuvir, characterized by a water vapor sorption isotherm showing a water uptake of not more than 0.15-0.25 wt %, preferably not more than 0.15 wt %, at a relative humidity of up to 90%. In a preferred aspect the present invention provides a solid form, preferrably a crystalline form, of sofosbuvir characterized by a water vapor sorption isotherm substantially as shown in FIG. 6.

In another aspect the present invention provides a solid form of sofosbuvir, preferably a crystalline form of sofosbuvir, characterized by a water vapor sorption isotherm showing a water uptake of not more than 0.10 wt %, at a relative humidity (RH) of up to 70% and/or a water uptake of not more than 0.15-0.25 wt %, preferably not more than 0.15 wt %, at a relative humidity of up to 90%.

In another aspect the present invention provides crystalline form E of sofosbuvir characterized by a water vapor sorption isotherm showing a water uptake of not more than 0.15-0.25 wt %, preferably not more than 0.15 wt %, at a relative humidity of up to 90%.

In another aspect the present invention provides crystalline form E of Sofosbuvir characterized by a water vapor sorption isotherm showing a water uptake of not more than 0.10 wt %, at a relative humidity (RH) of up to 70% and/or a water uptake of not more than 0.15-0.25 wt %, preferably not more than 0.15 wt %, at a relative humidity of up to 90%.

In another aspect the present invention provides crystalline form E of Sofosbuvir of low hygroscopicity characterized by a water vapor sorption isotherm showing a water uptake of not more than 0.15-0.25 wt %, preferably not more than 0.15 wt %, at a relative humidity of up to 90%.

In another aspect the present invention provides crystalline form E of sofosbuvir of low hygroscopicity characterized by a water vapor sorption isotherm showing a water uptake of not more than 0.10 wt %, at a relative humidity (RH) of up to 70% and/or a water uptake of not more than 0.15-0.25 wt %, preferably not more than 0.15 wt %, at a relative humidity of up to 90%.

In another aspect the invention relates to a process for preparing crystalline form E of sofosbuvir comprising (a) combining sofosbuvir with a solvent system comprising an organic solvent and optionally water (b) optionally seeding with form E crystals (c) adding an anti-solvent (d) optionally isolating crystalline form E and (e) optionally milling or micronizing to obtain crystalline form E of sofosbuvir having a smaller particle size. The process may also comprise filtering and drying steps.

Preferred organic solvents in step (a) may be selected from a group consisting of aliphatic ethers, preferable C4-C8 ethers, cyclic ethers, ketones, preferably C3-C8 ketones, alcohols preferably C4-C8 alcohols More preferably the organic solvents may be selected from a group consisting of Methyl t-butyl ether, t-Butanol, acetone, Methyl isobutyl ketone. Most preferably the organic solvent is Methyl isobutyl ketone.

Preferred solvent used as antisolvent in step (c) may be selected from a group consisting of aliphatic ethers, preferable C4-C8 ethers, alkanes, preferably C3-C8 alkanes, and cycloalkanes. More preferably the antisolvents may be selected from a group consisting of di-isopropyl ether, n-heptane, cyclohexane. Most preferably, the antisolvent is cyclohexane.

In a preferred embodiment step (a) is performed in a solvent system comprising an organic solvent and water. More preferably the amount of water may be in the range of 0%-2% by volume.

Preferably, reaction mixture of step (a) includes about 10% to about 50% of Sofosbuvir, by volume. Preferably, the process according to the present invention is carried out at temperatures between 0 to 20° C., more preferably between 0-15° C., most preferably 6-12° C.

The solution obtained in step (a) can be filtered, if desired, to dispose of foreign particles, while maintaining the filtered solution and filtrate at almost the same temperature. Preferably the process of the present invention is performed with stirring Typically, the amount of crystalline form E of Sofosbuvir used for seeding in step (b) is about 0.1% to 0.5% by weight of the Sofosbuvir.

The crystalline form E of sofosbuvir can be isolated by any method known in the art. For example, the crystalline form E of Sofosbuvir can be separated by filtering the slurry or decanting the solvent from the slurry. The isolating method can further comprise washing and drying the crystalline form E of sofosbuvir. Preferably, crystalline form E of Sofosbuvir is dried at a temperature of about 30° C. to about 60° C., more preferably, at a temperature of about 40° C. to about 50° C. under reduced pressure.

Crystalline form E of Sofosbuvir, can be milled or micronized to obtain sofosbuvir having a smaller particle size in a process that is adapted to the desired particle size. For example, micronization can be performed using a 100 mm plate airjet microniser.

In another aspect the invention provides a process for preparing crystalline form E of Sofosbuvir comprising: a) combining Sofosbuvir with methyl isobutyl ketone and water at b) seeding with form E crystals, c) adding cyclohexane d) optionally isolating form E and (e) optionally milling or micronizing to obtain crystalline form E of sofosbuvir having a desired particle size. The process may also comprise filtering and drying steps.

In one embodiment the starting material used in the above described process is crystalline form 1 of Sofosbuvir.

In another embodiment the amount of water in step a) may be in the range of 0.5 to 2% (by volume) and the reaction mixture is stirred. Preferably the amount of water is 1% (by volume) and the reaction is stirred at 50-200 RPM. The reaction mixture may be further filtered.

In yet another embodiment step a) is carried out at a temperature ranging from 0 to 20° C., preferably step a) is performed at 9±3° C.

In a preferred embodiment the invention provides a process for preparing crystalline form E of Sofosbuvir comprising: a) combining Sofosbuvir with Methyl isobutyl ketone and water wherein the amount of water is 1% by volume and the temperature is 9±3° C. b) seeding with form E crystals, c) adding cyclohexane d) isolating form E and (e) optionally micronizing. The process may also comprise filtering and drying steps.

In a preferred embodiment step a) may be performed with stirring at a rate of 50-200 RPM In a preferred embodiment the solution is stirred after seeding, stirring rate maybe in the range of 50-200 RPM.

In the most preferred embodiment, crystalline form 1 of sofosbuvir is combined with MIBK and water (1% by volume) at 9±3° C. The resulting suspension is stirred at 50-200 RPM until the solution becomes clear. The solution is filtered to remove any foreign particles. The filtered solution is charged, stirred at 9±3° C., seeded with Form E crystals and stirred as such for 4±0.5 h. Cyclohexane is then added and solution is stirred for 1±0.5 h at 9±3° C. Slurry is filtered and the cake is washed with cyclohexane. The obtained solid was dried under vacuum for 12 h at Tj 40-50° C. to afford Sofosbuvir Form E.

In another aspect the invention relates to crystalline form E produced by the above described process.

In another aspect the invention encompasses micronized or small particle size crystalline form E of sofosbuvir having a desired PSD which is suitable for preparation of pharmaceutical compositions and formulation for example d(0.1) 0.4-0.6 microns, d(0.5) 1.0-2.0 microns and d(0.9) 3.2-5.0 microns.

The small particle size sofosbuvir may be directly obtainable by different processes, for example it may be obtained through chemical synthesis or by micronization techniques, optionally using delumping techniques.

Micronization is a technique known to the skilled person. E.g., by milling as a commonly known micronization technique small particles sizes can be achieved.

It is generally known in the art that micronized or small particle size material may lead to downstream processing problems related to poor flow and dispersion properties. It was surprisingly found that the micronized or small particle size Sofosbuvir comprising crystalline form E of the present invention exhibits good flowability and compressibility and reduced hygroscopicity, therefore it can be advantageously used for preparation of pharmaceutical compositions and formulations.

The physical attributes of the API are especially critical for the reproducibility of preparation of dosage forms with high API content. A high drug load may pose flow problems (http://en.wikipedia.org/wiki/Power_flow" \o "Power flow) or require large dosage forms if the compound has low compressibility. Therefore, the micronized or small particle size crystalline form E of sofosbuvir of the present invention is suitable for use in the preparation of formulations containing high load of sofosbuvir, for example containing more than 35% of sofosbuvir. Further, the micronized or small particle size crystalline form E of sofosbuvir of the present invention is particularly suitable for use in the preparation of dry formulations containing high dosage of sofosbuvir as a sole API or in combination with another active pharmaceutical ingredient, for example, ledipasvir.

In one embodiment the invention encompasses micronized or small particle size Sofosbuvir comprising crystalline form E of sofosbuvir having preferred flowability properties, i.e. exhibiting a flow rate of not more than 100 sec/100 g, more preferred not more than 80 sec/100 gr, more preferred not more than 65 sec/100 g, as measured by flow-to-an-orifice in Pharma-Test 41-03300 automated powder testing system.

In another embodiment the invention encompasses micronized or small particle size crystalline form E of sofosbuvir having advantageous compressibility properties, i.e. exhibiting a constant density of not less than 0.40 g/ml, preferably not less than 0.43 g/ml, more preferably not less than 0.48 g/ml as measured at 0.2 MPa.

In another embodiment the invention encompasses micronized or small particle size crystalline form E of sofosbuvir characterized by a water sorption of not more than 0.5%, more preferably not more than 0.3% as measured by DVS and water content after equilibration at 90% RH.

Micronized or small particle size crystalline form E of sofosbuvir can be characterized by any one of the above aspects or any combination thereof.

In yet another preferred embodiment, the invention encompasses micronized or small particle size crystalline form E characterized by PSD of d(0.1) 0.4-0.6 microns, d(0.5) 1.0-2.0 microns and d(0.9) 3.2-5.0 microns; a flow rate of not more than 100 s/100 g, more preferred not more than 80 s/100 gr, more preferred not more than 65 sec/100 g; a constant density of not less than 0.40 g/ml, preferably not less than 0.48 g/ml as measured at 0.2 MPa; and a water sorption of not more than 0.5%, more preferably not more than 0.3% as measured by DVS and water content after equilibration at 90% RH.

In particularly preferred embodiment, the invention encompasses micronized or small particle size crystalline form E characterized by PSD of d(0.1) 0.4-0.6 microns, d(0.5) 1.0-2.0 microns and d(0.9) 3.2-5.0 microns; a flow rate of not more than 65 sec/100 g; a constant density of not less than 0.48 g/ml as measured at 0.2 MPa; and a water sorption of more than 0.3% as measured by DVS and water content after equilibration at 90% RH.

The above described micronized or small particle size form of Sofosbuvir can be used to prepare a pharmaceutical compositions and formulations.

The present invention comprises pharmaceutical compositions and formulations comprising crystalline form E of Sofosbuvir of the present invention, particularly formulations containing high load of sofosbuvir, for example containing more than 35% of sofosbuvir. Typically, the pharmaceutical composition is a solid composition and the Sofosbuvir retains its solid state form. The pharmaceutical composition may comprise sofosbuvir as a sole API or in combination with another active pharmaceutical ingredient, for example, ledipasvir. The pharmaceutical compositions can be prepared by a process comprising combining the crystalline form of Sofosbuvir of the present invention with at least one pharmaceutically acceptable excipient.

The above crystalline forms of Sofosbuvir of the present invention can also be used as medicaments.

The present invention further encompasses 1) the use of the above-described crystalline form of Sofosbuvir in the manufacture of a pharmaceutical composition, and 2) a method of treating a subject suffering from Hepatitis C, or otherwise in need of the treatment, comprising administration of an effective amount of a pharmaceutical composition comprising the above crystalline form of Sofosbuvir described herein.

Solid pharmaceutical compositions according to the present invention are, e.g., powders, granules, pellets, capsules or tablets.

The pharmaceutical composition of the present invention is preferably in form of a tablet comprising one or more pharmaceutically acceptable excipients. The tablet is for oral use.

The pharmaceutical compositions in the form of a tablet according to the present invention are preferably for use in treating hepatitis C virus infections as is known in the art. As indicated above, in such a use the compositions in the form of a tablet according to the present invention can be used alone or in the form of a combination therapy as is known in the art.

Processes for preparing the pharmaceutical compositions in the form of a tablet according to the invention are known in the art. The sofosbuvir may be dry-granulated or wet-granulated before tableting, or the tablet blends may be directly compressed. Granulation is preferred for preparing sofosbuvir tablets, and dry granulation is most preferred. Tablets in accordance with the invention may be coated to facilitate swallowing and/or to enhance the appearance of the tablet.

In a preferred embodiment the pharmaceutical compositions in the form of a tablet according to the present invention are prepared by dry granulation. It is preferred that in the dry granulation method first a comprimate is formed, the comprimate is then crushed in order to obtain particles which are easier to handle than the original mixture. The crushed particles are sieved, optionally blended in a mixer such as a tumble mixer and then pressed to the pharmaceutical composition in the form of a tablet as described herein.

Preferably the pharmaceutical composition according to the present invention comprise small particle size sofosbuvir, preferably the small particle size crystalline sofosbuvir is crystalline small particle size form E sofosbuvir. In another embodiment the pharmaceutical composition comprises small particle size sofosbuvir and no glidants.

Glidants are known to the skilled person. They reduce interparticle friction and cohesion and thus increase flowability of particles or mixtures. Colloidal silicon dioxide is the most known glidant. In contrast to glidants, lubricants prevent ingredients from sticking to e.g. tablet punches. Magnesium stearate is a typical lubricant (not a glidant).

The composition comprising small particle size sofosbuvir preferably comprises not more than 1.5% of lubricants based on the weight of the total composition. In particular, the composition of the present invention preferably comprises not more than 1.5% of magnesium stearate, more preferably not more than 1%, mostly preferred not more than 0.6% of magnesium stearate based on the weight of the total composition. For the pharmaceutical compositions comprising small particle size sofosbuvir and no glidants, particle size distribution is measured by laser diffraction, and preferably refers to a volume distribution. Preferably particle size distribution is measured using the Malvern Mastersizer 2000. The small particle size sofosbuvir preferably has a d(0.5) of less than 20 μm, preferably less than 10 μm, more preferably less than 5 μm and most preferably between 1-2 μm. In one embodiment, the small particle size sofosbuvir has a d(0.1) of 0.4-0.6 μm, a d(0.5) of 1.0-2.0 μm and a d(0.9) of 3.2-5.0 μm. The d(0.1), d(0.5) and d(0.9) values are based on a volume distribution. For measurement of the sofosbuvir particle size it is also referred to Example 22.

Having thus described the invention with reference to particular preferred embodiments and illustrative examples, those in the art can appreciate modifications to the invention as described and illustrated that do not depart from the spirit and scope of the invention as disclosed in the specification. The Examples are set forth to aid in understanding the invention but are not intended to, and should not be construed to limit its scope in any way.

Methods

X-Ray Powder Diffraction (Examples 1-13)

X-ray powder diffraction analyses were performed on X-Ray powder diffractometer Bruker D8 Advance; CuKα radiation (λ=1.5418 Å); Lynx eye detector; laboratory temperature 22-25° C.; PMMA specimen holder ring. Prior to analysis, the samples were gently ground by means of mortar and pestle in order to obtain a fine powder. The ground sample was adjusted into a cavity of the sample holder and the surface of the sample was smoothed by means of a cover glass.

Measurement Parameters:
  Scan range: 2-40 degrees 2-theta;
  Scan mode: continuous;
  Step size: 0.05 degrees;
  Time per step: 0.5 s;
  Sample spin: 30 rpm;
  Sample holder: PMMA specimen holder ring.

The described peak positions were determined using silicon powder as an internal standard in an admixture with the sample measured. The position of the silicon (Si) peak was corrected to silicone theoretical peak: 28.45 degrees two-theta, and the positions of the measured peaks were corrected respectively.

DVS Measurements

DVS measurements were performed SMS DVS instrument

Analysis Parameters:
  Mass: 20-30 mg
  Temperature: 25° C.
  Humidity range: 0%-90%-0% cycle.
  Step size: 10% RH
  dm/dt: 0.002%/min
  minimum step duration: 60 min
  maximum step duration: 720 min
  Flowability The flow rate (sec/100 gr powder) was measured in Pharma-Test 41-03300 flowmeter. The apparatus consists of conical stainless steel powder funnel on the top of the apparatus equipped with automated stirring blade and a 15 mm pouring nozzle below the funnel. The method consists of pouring a quantity of powder under stirring regime through a given size nozzle, and weighing the weight of the powder that passed through the nozzle and the time it took. Results are given as sec/100 gr.

Method of PSD Measurements of Form 7

If a wet measurement is used the particles to be measured are dispersed in a dispersant, preferably a dispersant having a refractive index (RI) of 1.403, and the measurement is carried out at 2000 rpm and ultrasound for 120 s prior to measurement. Preferably, unless otherwise indicated the particle size distribution is determined using a wet measurement using a Mastersizer 2000 from Malvern Instruments and Malvern Hydro 2000S wet sample dispersion unit and silicone oil as dispersant. Unless otherwise indicated, the following settings are preferably used:

| | |
|---|---|
| Number of measurement cycles | 3 |
| Analysis model | Fraunhofer |
| Obscuration | 5-15% |
| Sample measurement time | 10 sec |
| Sonication time | 120 s before measurement |
| Stirrer speed | 2000 rpm |
| Dispersant RI (silicone oil) | 1.403 |

Method for PSD Measurement of Form E—
  Dry cell measurement
  Mastersizer 2000
  Analysis model: General purpose
  Powder RI: 1.573
  Absorption: 0.5
  Dispersant name: Dry Dispersion (Air)
  Dispersant RI: 1.0
  Sensitivity: Normal (fine powder)
  Filtering obscuration: On (0.5-3%)
  Measuring time: 5 seconds (5000 snaps)
  Background measuring time: 5 seconds (5000 snaps)
  Repeats aliquots: 1
  Repeat Measurements: 1
  Pressure: 2.5 Bar
  Feed rate of the flow cell: 30%
  Funnel gap: 5 mm
  Feeder with small sieve filled with balls (⅔ by volume)
  Between samples runs, clean the cell with air for 30 seconds.
  A background measurement should be performed before each measurement.
  Add about 0.5 gm sofosbuvir powder with a spatula directly into the feeder. Start the feeder work. The obscuration should be in the range 0.5-3%.

EXAMPLES

For Examples 1-13, Sofosbuvir was prepared according to the method described in B. S. Ross, P. G. Reddy, H.-R. Zhang, S. Rachakonda, M. J. Sofia, J. Org. Chem. 2011, 76, 8311. Form 1 of Sofosbuvir may be obtained according to the process described in WO 2010/135569.

Example 1

Preparation of Crystalline Form E of Sofosbuvir

Sofosbuvir (1 g, Form 1) was dissolved in the acetone (3 mL) under stirring at 25±5° C. Then di-iso-propyl-ether (DIPE) (10 mL) was added under stirring to get turbidity. The mass was stirred for 2 h at 25±5° C. to give a white solid. To this mass DIPE (15 mL) was added and the mass was stirred for 48 h at 25±5° C. The mass was filtered and the obtained solid was dried at 50° C. under vacuum for 12 h to provide form E of Sofosbivir (as confirmed by XRPD).

Example 2

Preparation of Crystalline Form E of Sofosbuvir

Methyl iso-butyl ketone (MIBK) (3 mL) was charged in 100 mL round bottom glass flask equipped with mechanical stirrer. This was cooled to 0 to 5° C. under stirring and Sofosbuvir (1 g, Form-1) was added at 0 to 5° C. This mass slowly became clear after 15 min at 0 to 5° C. At this point, seeds of Sofosbuvir Form E (10 mg) were added at the same temperature. After 10 min of stirring at the same temperature, formation of precipitate was observed. The mass was stirred for 1 h at 0 to 5° C. Cyclohexane (10 mL, precooled to 15° C.) was added and stirred for 2 to 5 min. The precipitate was filtered and washed with cyclohexane (10 mL, precooled to 15° C.). The solid was dried at 33° C. under vacuum for 12 h, to provide form E of Sofosbivir (as confirmed by XRPD).

Example 3

Preparation of Crystalline Form E of Sofosbuvir

MIBK (60 mL) was charged in 250 mL round bottom glass flask equipped with mechanical stirrer. This was cooled to 10 to 15° C. under stirring and Sofosbuvir (20 g, Form 1) was added at 10 to 15° C. This mass slowly became clear after 20 min at 10 to 15° C. At this point, seeds of Sofosbuvir Form E (100 mg) were added at the same temperature. After 10 min of stirring at the same temperature, formation of precipitate was observed. The mass was stirred for 1 h at 10 to 15° C. Cyclohexane (60 mL, precooled to 15° C.) was added slowly and stirred for 2 to 5 min. The precipitate was filtered and washed with cyclohexane (60 mL, precooled to 15° C.). The obtained solid was dried at 33° C. under vacuum for 12 h, to provide form E of Sofosbivir (as confirmed by XRPD).

Example 4

Preparation of Crystalline Form E of Sofosbuvir

MIBK (3 mL) was charged in 100 mL round bottom glass flask equipped with mechanical stirrer. This was cooled to 10 to 15° C. under stirring and Sofosbuvir (1 g, Form 1) was added at 10 to 15° C. This mass slowly became clear after 15 min at 10 to 15° C. At this point, seeds of Sofosbuvir Form E (10 mg) were added at the same temperature. After 10 min of stirring at the same temperature, formation of precipitate was observed. The obtained mass was stirred for 1 h at 10 to 15° C. Cyclohexane (10 mL, precooled to 15° C.) was added and stirred for 2 to 5 min. The obtained precipitate was filtered and washed with cyclohexane (10 mL, precooled to 15° C.). The solid was dried at 33° C. under vacuum for 12 h, to provide form E of Sofosbivir (as confirmed by XRPD).

Example 5

Single Crystal X-Ray Crystallography of Form E

Sofosbuvir form E was sealed in 1 mm capillaries (1257-67A), glass No. 50. Powder diffraction pattern was measured using synchrotron radiation at wavelength 0.40003(1) Å. The reflection positions were determined in DASH software and indexation was done in DICVOL91 software. Structure was solved by DASH 3.2 program. The structure refinement from powder was done in JANA2006 software. Presence of any solvent was not detected.

Lattice Parameters for Sofosbuvir, Form E:

| | |
|---|---|
| cell_length_a | 14.4723(2) Å |
| cell_length_b | 17.0212(2) Å |
| cell_length_c | 5.22862(6) Å |
| cell_angle_alpha | 90.0000° |
| cell_angle_beta | 100.297(1)° |
| cell_angle_gamma | 90.0000° |
| cell_volume | 1267.3 Å3 |
| symmetry_space_group_name_ | P21 |
| symmetry_cell_setting | monoclinic |
| cell_measurement_temperature | 293 K |

Example 6

Preparation of Crystalline form E of Sofosbuvir

Sofosbuvir Form 1 (100 g) along with MIBK (500 mL) was charged in 4-neck round bottom flask equipped with mechanical stirrer. Moisture content of the reaction was adjusted to 0.5-2.0% by volume and material was dissolved under stirring at 10+5° C. Sofosbuvir Form E crystals (1 g) were added to the reaction flask and stirring was continued at the same temperature. During this interval, white solid slowly precipitated out from the reaction mixture. After 4-7 hours, cyclohexane (1000 mL) was added and resulting slurry was filtered. White solid obtained was washed with cyclohexane (2×200 mL) and dried 45° C. under vacuum for 12 h to yield Form E of sofosbuvir (as confirmed by XRPD).

Example 7

Preparation of Crystalline Form E of Sofosbuvir

MIBK (5 L) and water (1% of MIBK) were added to Sofosbuvir Form-1 (1 Kg) at 9±3° C. The resulting suspension was stirred at 50-200 RPM until the solution becomes clear. Solution was filtered to remove any foreign particles. Washed with MIBK (0.5 L). The filtered solution was charged, stirred at 9±3° C., seeded with Form E crystals and solution was stirred as such for 4±0.5 h at 50-200 RPM. Cyclohexane (10 L) was then added and solution was stirred for 1±0.5 h at 9±3° C. Slurry was filtered and the cake was washed with cyclohexane (2×2 L). Solid was dried under vacuum for 12 h at Tj 40-50° C. to afford Sofosbuvir Form E in 80 to 90% yield.

Example 8

Preparation of Micronized Crystalline Form E of Sofosbuvir

Micronized crystalline form E of sofosbuvir was prepared using a 100 mm plate airjet microniser, feed rate 0.5 Kg/hr, feeding pressure is 6.5 bars+/−0.5 bar, milling pressure is 6 bars+/−0.5 bar.

Example 9

Flowability of Micronized Crystalline Form E of Sofosbuvir 70 gr of the powder of micronized crystalline form E of Sofosbuvir obtained according to Example 8, was poured in the funnel. Stirring at 20 rpm was started, the pouring nozzle opened and the powder started flowing through the nozzle. After approximately 30 seconds the flow was interrupted. The exact weight of the powder which passed through the orifice and the exact time in seconds were automatically recorded. The resulting flow rate, measured in duplicate analyses, was: 63 sec/100 gr and 62 sec/100 mg.

Example 10

Compressibility of Micronized Crystalline Form E of Sofosbuvir

Compression profiles were obtained using a die and a flat-faced punch fitted on a TA-XT2 Texture analyser (Stable Micro Systems Ltd., Godalming, UK).

200 mg of micronized crystalline form E of Sofosbuvir obtained according to example 8 is compressed in a steel mould (with the rate of displacement 0.03 mm/s). Cyclic procedure (similar to tapping) was performed: compressing, then retracting, relaxation for 15 s and then repeated compressive steps (altogether 10 steps). Each step exerts 0.2 MPa pressure on to the sample. Sample density is calculated by dividing the weight by the sample volume for each cycle. Maximum density is reached within 10 steps. The maximal compressive displacement was 0.5 mm. The resulting density was: 0.48 g/ml

Example 11

Preparation of Crystalline Form E of Sofosbuvir

Sofosbuvir (Form 1, 1 g) was suspended in methyl tert-butyl ether (MTBE) (20 mL) and stirred for 2 hrs at 25±5° C. The slurry was heated to 50° C. for 3 hrs and then bought to 25±5° C. n-Heptane (10 mL) was added and the reaction mixture was stirred for 72 hrs at 25±5° C. The mass was then filtered and the obtained solid was dried at 50° C. under vacuum for 12 hrs, to provide form E of Sofosbuvir (as confirmed by XRPD).

Example 12

Preparation of Crystalline Form E of Sofosbuvir

Sofosbuvir (Form 1, 1 g) was dissolved in the t-butanol (3 mL). Then n-hexane (8 mL) was added, the mass was stirred for 24 hrs at 25±5° C. to provide a white solid. The mass was filtered and the obtained solid was dried at 50° C. under vacuum for 12 hrs. to provide form E of Sofosbuvir (as confirmed by XRPD).

Example 13

Preparation of Crystalline Form E of Sofosbuvir

Sofosbuvir (Form 1, 1 g) was dissolved in methyl isobutyl ketone (MIBK) (4 mL). Then cyclohexane (4 mL) was added, and the obtained mass was stirred for 24 hrs at 25±5° C. to provide a white solid. The mass was filtered and the obtained solid was dried at 50° C. under vacuum for 12 hrs to provide form E of Sofosbuvir (as confirmed by XRPD, FIG. 1 and FIG. 7).

X-Ray Powder Diffraction (Examples 14 and 15)

Sample were measured on a D8 Advance powder X-ray diffractometer (Bruker AXS, Karlsruhe, Germany) in a rotating PMMA sample holder (diameter: 25 mm; depth: 1 mm) in reflection mode (Bragg-Brentano geometry). Raw data were analyzed with the program EVA (Bruker AXS, Karlsruhe, Germany). Background subtraction and Kα2 stripping were not performed with the diffractograms shown in FIG. 2 and FIG. 8. Peak intensities (FIG. 9) were determined after background subtraction.

Measurements Conditions:

| | |
|---|---|
| radiation | Cu Kα1/α2 |
| source | 34 kV/40 mA |
| detector | Vantec-1 (electronic window: 3°) |
| Kβ filter | Ni (diffracted beam) |
| measuring circle diameter | 435 mm |
| detector window slit | 12 mm |
| anti-scatter slit (diffracted beam) | 8 mm |
| divergence slit | v6.00 (variable) |
| Soller slit (incident/diffracted beam) | 2.5° |
| 2θ range | $2° \leq 2\theta \leq 55°$ |
| step size | 0.016 |
| step time | 0.2 s |

For Examples 14 and 15, Sofosbuvir was prepared according to the method described in B. S. Ross, P. G. Reddy, H.-R. Zhang, S. Rachakonda, M. J. Sofia, J. Org. Chem. 2011, 76, 8311. Form 1, described in US 2011/251152, was obtained by crystallization of the product from dichloromethane solution at room temperature.

Example 14

Preparation of Crystalline Form 7 of Sofosbuvir

Form 1 of Sofosbuvir (200 mg) was stored as a powder in an open glass vial at 40° C./75% relative humidity. After 4 weeks an amorphous solid had formed. This solid crystallized during continued storage at 40° C./75% relative humidity after an additional period of 4 weeks. Form 7 was obtained as a colourless solid in quantitative yield.

The X-Ray Powder Diffractogram of Form 7 is Depicted in FIG. 8.

Example 15

Preparation of Crystalline Form 7 of Sofosbuvir

Form 1 of Sofosbuvir (1.04 g) was heated in deionized water (40 mL) at 50° C. for 2 hours under stirring. Partial dissolution occurred and the remaining solid changed into a sticky mass. No crystallization was observed. Approximately 10 mg of Form 7 (obtained from the procedure of Example 14) were added and the mixture was cooled at room temperature. Crystallization of Form 7 occurred during storage overnight. A small amount of sticky mass remained on the stirring bar, which was removed mechanically. Form 7 was isolated by filtration and dried in an evacuated desiccator over silica gel.

X-Ray Powder Diffraction (Examples 16-20)

Samples were measured on a D8 Advance powder X-ray diffractometer (Bruker AXS, Karlsruhe, Germany) in a rotating PMMA sample holder (diameter: 25 mm; depth: 1 mm) in reflection mode (Bragg-Brentano geometry). Conditions of the measurements are summarized in the table below. Raw data were analyzed with the program EVA (Bruker AXS, Karlsruhe, Germany). Background subtraction and Kα2 stripping were not performed with the diffractogram shown in the FIG. 10. Peak intensities were determined after background subtraction.

| | |
|---|---|
| Radiation | Cu Kα1/Kα2 ($\lambda$ = 1.54187 Å) |
| Source | 34 kV/40 mA |
| Detector | Vantec-1 (electronic window: 3°) |
| Kβ filter | Ni (diffracted beam) |
| Measuring circle diameter | 435 mm |
| Detector window slit | 12 mm |
| Anti-scatter slit (diffracted beam) | 8 mm |
| Divergence slit | V6.00 (variable) |
| Soller slit (incident/diffracted beam) | 2.5° |
| 2θ range | $2° \leq 2\theta \leq 55°$ |
| Step size | 0.016 |
| Step time | 0.2 s |

Reference Examples A-C for Examples 16-21

A. Sofosbuvir Starting Material (Form 1)

Form 1 Sofosbuvir was prepared by crystallisation of Sofosbuvir from dichloromethane according to the method described in B. S. Ross, P. G. Reddy, H.-R. Zhang, S. Rachakonda, M. J. Sofia, J. Org. Chem. 2011, 76, 8311 (page 8311). The Form 1 Sofosbuvir is characterised by XRPD peaks at approximately 5.0, 7.3, 9.4, 18.1±0.2 degrees 2-theta. Form 1 may be further characterised by additional XRPD peaks at approximately 8.8, 10.0, 11.4, 15.0 and 22.3 degrees 2-theta±0.2 degrees 2-theta.

B. Preparation of Form 7 Sofosbuvir Seed Crystals (i) Small amounts of Form 7 Sofosbuvir, which were used as seed crystals, were prepared in the following way: Form 1 of Sofosbuvir (200 mg) was stored as a powder in an open glass vial at 40° C./75% relative humidity. After storage for 8 weeks at 40° C./75% relative humidity, Form 7 was obtained as a colourless solid in quantitative yield.

(ii) Form 7 was prepared by heating Form 1 of Sofosbuvir (1.04 g) in deionized water (40 mL) at 50° C. for 2 hours with stirring. Partial dissolution occurred and the remaining solid changed into a sticky mass. No crystallization was observed. Approximately 10 mg of Form 7 [obtained from (i)] was added and the mixture was cooled to room temperature. Crystallization of Form 7 occurred during storage overnight. A small amount of sticky mass remaining on the stirring bar, which was removed mechanically. Crystalline Form 7 was isolated by filtration and dried in an evacuated desiccator over silica gel.

C. Preparation of Water-Saturated MTBE (Methyl Tert-Butyl Ether)

Water-saturated MTBE was prepared by vigorous stirring (500 rpm) of MTBE with deionized water in a volume ratio of 10:1 for 30 minutes at room temperature and subsequent phase separation to remove the aqueous layer. The organic phase was prepared freshly before use. Alternatively, the organic phase may be stored in a sealed container at ambient temperature.

Example 16

Preparation of Form 7 Sofosbuvir

Sofosbuvir (50 g) was dissolved almost completely in water-saturated MTBE (800 ml) at room temperature. The solution was filtered through a folded filter. Seed crystals of Sofosbuvir Form 7 (150 mg) were added and the solution was stored for two days in a closed flask at room temperature without stirring. The formed crystals (Form 7) were isolated by filtration, washed with a small amount of MTBE, and dried at room temperature under vacuum (2 mbar) overnight. The yield was 23.9 g. The mother liquor was concentrated to a volume of 350 ml on a rotary evaporator and then stored for two days in a closed flask at room temperature without stirring. During this time, the initially separated oil crystallised. The formed solid (Form 7) was then isolated by filtration, washed with a small amount of MTBE, and dried at room temperature under vacuum (2 mbar) overnight. The weight of the solid (Form 7) was 15.7 g. Hence the combined yield of Form 7 was 39.7 g (79%).

Example 17

Preparation of Form 6 Sofosbuvir, Small Scale

Sofosbuvir (2 g) was dissolved almost completely in water-saturated MTBE (30 ml) at room temperature. The solution was filtered through a folded filter and was magnetically stirred (400 rpm) for 12 h in a closed flask at room temperature. The formed crystals (consisting of Form 6) were isolated by filtration, washed with a small amount of MTBE, and dried at room temperature under vacuum (2 mbar) overnight. The yield was 1.2 g (60%).

Example 18

Preparation of Form 6 Sofosbuvir

Sofosbuvir (40 g) was dissolved almost completely in water-saturated MTBE (600 ml) at room temperature. The solution was filtered through a folded filter. Seed crystals of Sofosbuvir Form 6 (100 mg, obtained from Example 17) were added and the solution was mechanically stirred (300 rpm) for 12 h in a closed flask at room temperature. The formed crystals (Form 6) were isolated by filtration, washed with a small amount of MTBE, and dried at room temperature under vacuum (2 mbar) overnight. The yield was 29.6 g (74%).

Example 19

Dissolution of Sofosbuvir Form 6 and Form 7

Figure 13:
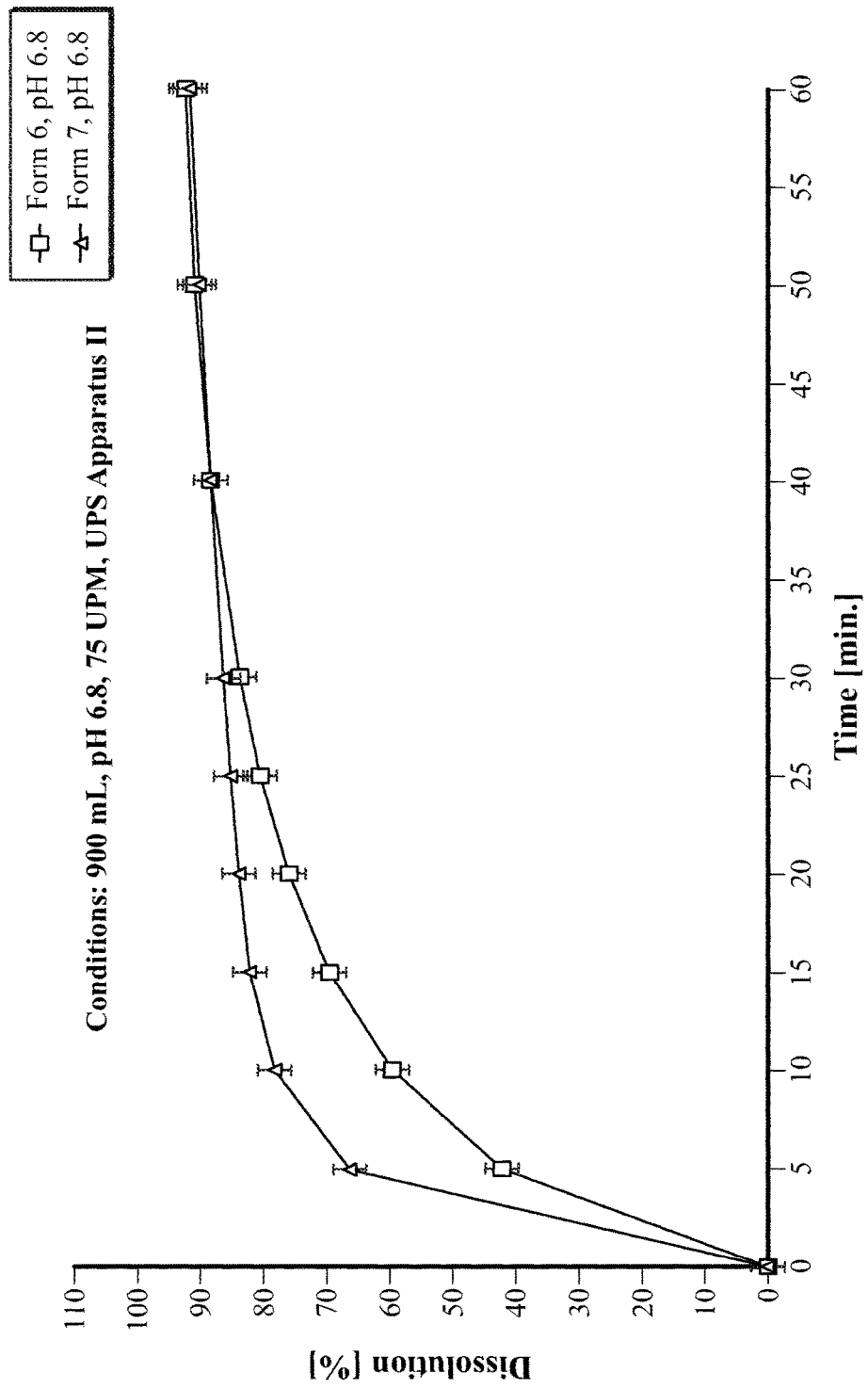
FIG. 13 shows the dissolution curves for Form 7 vs Form 6 measured in 50 mM phosphate buffer (pH 6.8, 900 mL) at 37° C., using USP apparatus II, paddle method according to the example described below.

Sofosbuvir form 6 prepared according to example 18 above and Sofosbuvir form 7 prepared according to example 16 above was used. The dissolution of Sofosbuvir Form 7 and Form 6 was measured (in triplicate) in 50 mM phosphate buffer at 37° C. (pH 6.8, 900 mL), using USP apparatus II, paddle method. Every 5 minutes, a probe was taken and measured by UV/VIS at 260 nm and path length 0.1 cm; UV/VIS was measured on an Agilent model 8453 with Chem Station Dissolution Software. 400 mg of Sofosbuvir Form 7 or Form 6 was used for the test, and the percentages are given in relation to 400 mg of the API. The results are represented graphically in FIG. 13.

Example 20

Solubility and Particle Size of Sofosbuvir Form 6 and Form 7

Sofosbuvir form 6 prepared according to example 18 above and Sofosbuvir form 7 prepared according to example 16 above was used.

The particle size distribution was determined using a wet measurement using a Mastersizer 2000 from Malvern Instruments and Malvern Hydro 2000S wet sample dispersion unit and silicone oil as dispersant. The following settings are used:

| | |
|---|---|
| Number of measurement cycles | 3 |
| Analysis model | Fraunhofer |
| Obscuration | 5-15% |
| Sample measurement time | 10 sec |
| Sonication time | 120 s before measurement |
| Stirrer speed | 2000 rpm |
| Dispersant RI (silicone oil) | 1.403 |

Results are given in the following table:

TABLE

| | Particle sizes (μm) of Form 7 and Form 6 | | |
|---|---|---|---|
| | $D_{10}$ | $D_{50}$ | $D_{90}$ |
| Form 7 | 4.9 | 31.3 | 100.6 |
| Form 6 | 2.0 | 8.2 | 22.9 |

The solubility was determined as follows:

100 mg test substance was weighed into a glass vial, followed by addition of 4 mL solvent (water, 0.01 M HCl, 20 mM sodium acetate/acetic acid [pH 4.5], 50 mM $KH_2PO_4$ [pH 6.8]). A stirring bar was added, the vial was fixed in a block heater at 37° C. and the suspension was stirred with 250 rpm. After 15 min and 1 h, samples were withdrawn and filtered through a 0.2 μm PTFE filter. 100 μL of the clear filtrate were diluted with 900 μL acetonitrile/water mixture (1:1) and 1 μL thereof was analyzed by UHPLC/UV:

Instrument: Agilent 1290 Infinity
Wavelength: 260 nm
Column: Phenomenex Kinetex XB—C18, 1.7 μm, 50×3 mm
Column temp.: 40.0° C.
Flow [mL/min]: 0.4
Injection volume: 1 μL
Solvent A: water+0.2% Formic acid+0.1% HFBA heptafluorobutyric acid)
Solvent B: acetonitrile
Gradient time [min] Solvent B [%]
0.00 30.0
7.00 70.0
7.10 30.0
10.00 30.0

Results are given in the following table:

TABLE

Solubilities [mg/mL] of Sofosbuvir Form 6 and Form 7 after 15 min and 1 h at 37° C.

|  | Form 7 | | Form 6 | |
| --- | --- | --- | --- | --- |
|  | 15 min | 1 h | 15 min | 1 h |
| water | 3.1 | 3.1 | 2.4 | 2.3 |
| 0.01 M HCl | 3.2 | 3.2 | 2.5 | 2.4 |
| 20 mM NaOAc/HOAc (pH 4.5) | 3.1 | 3.1 | 2.4 | 2.5 |
| 50 mM $KH_2PO_4$ (pH 6.8) | 3.2 | 3.0 | 2.3 | 2.3 |

The solubility of Form 7 measured in physiologically relevant solvents at 37° C. after 15 min and after 1 hour is approximately one third higher than the solubility of Form 6. This result is particularly surprising in view of the fact that the particle size of the examined batch of Form 7 is distinctly larger than that of Form 6. Hence Form 7 provides a significant advantage regarding its solubility behavior.

Example 21

Single Crystal Data for Sofosbuvir Form 7

Crystals of Sofosbuvir Form 7 were obtained by the procedure of Example 16. A small prism was selected as a suitable twinned crystal, since a single crystal of sufficient volume could not be found. Data were collected on a Gemini Atlas CCD diffractometer (Cu Kα) using ω scans. Data collection runs were optimized for absolute configuration analysis. Positional and anisotropic thermal parameters of all non-hydrogen atoms were refined. The H atoms attached to carbon were placed geometrically. The positions of H atoms were refined with soft restraints on bond lengths and angles to regularise their geometry (C—H in the range 0.93-0.98). The positions of hydrogen atoms attached to nitrogen and oxygen were initially refined with restrained bond lengths and then with riding constraints. $U_{iso}(H)$ was set in the range of 1.2-1.5 times $U_{eq}$ of the parent atom. The contributions of twin component 1, twin component 2, inverted component 1, and inverted component 2 were refined to 0.60(4), 0.42(3), 0.00(4), and 0.03 (3), hence the assignment of the absolute configuration is correct. No residual solvent accessible voids were reported by the Platon void calculation routine.

Employed Software:

Data collection: CrysAlisPro CCD (Oxford Diffraction Ltd, 68 Milton Park, Abingdon, Oxfordshire OX14 4RX, England, Version 171.31.7, 2002);

cell refinement: CrysAlisPro RED;

data reduction: CrysAlisPro RED;

program used to solve structure: Superflip [Palatinus L. & Chapuis G. (2007). J. Appl. Cryst. 40, 786-790];

program used to refine structure and absolute configuration analysis: *Crystals* [Betteridge, P. W., Carruthers, J. R., Cooper, R. I., Prout, K. & Watkin, D. J. (2003). J. Appl. Cryst. 36, 1487]; Molecular graphics: *Mercury;* void calculation was done by Platon [Spek, A. L. (2003). PLATON, A Multipurpose Crystallographic Tool, Utrecht University, Utrecht, The Netherlands]

| | |
| --- | --- |
| Temperature | 120 K |
| Wavelength | Cu Kα |
| Crystal system | monoclinic |
| Space group | $P2_1$ |
| Unit cell dimensions | |
| a [Å] | 5.1667 (10) |
| b [Å] | 16.8545 (10) |
| c [Å] | 14.440 (10) |
| β [°] | 100.189 (10) |
| Volume [Å$^3$] | 1237.6 (3) |
| Z | 2 |
| Density (calculated) [g · cm$^{-3}$] | 1.418 |
| Absorption coefficient [mm$^{-1}$] | 1.56 |
| F (000) | 554 |
| Crystal size [mm] | 0.40 × 0.06 × 0.04 |
| Theta range for data collection | 4.1 to 67.0 |
| Index ranges | −6 ≤ h ≤ 6, −19 ≤ k ≤ 19, 0 ≤ l ≤ 17 |
| Reflections collected | 4269 |
| Independent reflections ($R_{int}$) | 4269 (0.049) |
| Completeness to Theta = 67.0° | 98.7% |
| Absorption correction | Semi-empirical from equivalents |
| $T_{min}$, $T_{max}$ | 0.61, 0.94 |
| Refinement method | Full-matrix least-squares on F$^2$ |
| Data/parameters/restraints | 4254/328/1 |
| Goodness-of-fit on F$^2$ | 0.9228 |
| Final R indices [I > 2σ(I)] | $R_1$ = 0.0525, $wR_2$ = 0.1375 |
| Final R indices [all data] | $R_1$ = 0.0549, $wR_2$ = 0.1458 |
| Largest diff. peak and hole [e · Å$^{-3}$] | 0.76, −0.50 |

Example 22

Pharmaceutical Compositions (e.g. Tablet) of Sofosbuvir

| | Sofosbuvir Form E formulation | Sofosbuvir Form 6 formulation |
| --- | --- | --- |
| Intragranular ingredients (mg) | | |
| Part I | | |
| Small particle size Sofosbuvir | 400 | 400 |
| Microcrystalline Cellulose | 215 | 215 |
| Croscarmellose Sodium | 30 | 30 |
| Mannitol | 270 | 270 |
| Silicon Dioxide | — | — |

-continued

|  | Sofosbuvir Form E formulation | Sofosbuvir Form 6 formulation |
|---|---|---|
| Part II |  |  |
| Magnesium stearate | 5 | 5 |
| Extragranular ingredients |  |  |
| Part III |  |  |
| Microcrystalline Cellulose | 45 | 45 |
| Croscarmellose Sodium | 30 | 30 |
| Part IV |  |  |
| Magnesium stearate | 5 | 5 |
| Silicon Dioxide | — | — |
| Total core weight | 1000 | 1000 |

Method of Preparation:

The batches were prepared by a dry granulation method. The intra-granular ingredients of Part I were blended for 10 minutes, Magnesium Stearate of Part II was added to the mix and blended for additional 5 minutes. The obtained blend was granulated by the roller compactor and milled through 0.8 mm screen and blended with the Part III extra-granular excipients for 10 minutes. Part IV Magnesium Stearate added to the blend and blended for additional 5 minutes. The final blend was compressed into tablets.

Physical Results

|  | Sofosbuvir Form E formulation | Sofosbuvir Form 6 formulation |
|---|---|---|
| Hausner Ratio | 1.22 | 1.22 |
| Carr's Index | 18 | 18 |
| Tablet Weight (mg) | 1000 | 1000 |
| Tablet Hardness (scu) | 41 | 40 |
| Disintegration Time (min) | 1:21 | 1:37 |

The Hausner ratio and Carr's is frequently used as an indication of the flowability of a powder. The Hausner factor is the ratio of bulk volume to compacted volume, calculated by the formula bulk density/tapped density. Bulk and tapped density are measured according to the general Pharmacopoeia method. Hausner ratio of <1.25 indicates a powder that is free flowing. A Carr's Index >23 indicates poor flow.

Further aspects and embodiments of the present invention are set out in the following numbered paragraphs:

1A. Crystalline form E of Sofosbuvir characterized by an X-ray powder diffraction pattern as depicted in any one of FIG. 1 or 2.

2A. Crystalline form E of Sofosbuvir optionally according to paragraph 1A characterised by an X-ray powder diffraction pattern having peaks at 12.4, 16.2, 17.2, 24.9 and 25.3 degrees two theta±0.2 degrees two theta and also having one, two, three, four or five peaks selected from: 8.1, 19.4, 22.0, 23.3 and 25.3 degrees two theta±0.2 degrees two theta.

3A. Crystalline form E of Sofosbuvir according to any of paragraphs 1A and/or 2A which is isolated.

4A. Use of crystalline form E of sofosbuvir according to any of paragraphs 1A, 2A and/or 3A to prepare a pharmaceutical composition or formulation.

5A. A pharmaceutical composition or formulation comprising a crystalline form E of Sofosbuvir according to any of paragraphs 1A, 2A, 3A and/or 4A.

6A. A pharmaceutical composition according to paragraph 5A which is a solid composition and the Sofosbuvir retains its solid state form.

7A. A process for preparing a pharmaceutical composition according to paragraph 5A and/or 6A comprising combining the crystalline form of Sofosbuvir according to any of paragraphs 1A, 2A and/or 3A with at least one pharmaceutically acceptable excipient.

8A. A crystalline form of Sofosbuvir according to any of paragraphs 1A, 2A and/or 3A for use as a medicament, preferably for the treatment of Hepatitis C.

9A. A method of treating a subject suffering from Hepatitis C, or otherwise in need of the treatment, comprising administration of an effective amount of a pharmaceutical composition comprising a crystalline form of Sofosbuvir as defined in any of paragraphs 1A, 2A and/or 3A.

1B. A crystalline form of Sofosbuvir, designated form E, characterized by data selected from one or more of the following: an X-ray powder diffraction pattern as depicted in FIG. 1; an X-ray powder diffraction pattern having peaks at: 12.4, 16.2, 17.2, 25.0 and 25.3 degrees two theta±0.1 degrees two theta; an X-ray powder diffraction pattern as depicted in FIG. 1; an X-ray powder diffraction pattern having peaks at: 12.4, 16.2, 17.2, 25.0 and 25.3 degrees two theta±0.1 degrees two theta and absence of peaks at: 10.9 and 14.2 degrees two theta±0.2 degrees two theta; and combinations of these data.

2B. A crystalline form E of Sofosbuvir according to paragraph 1B which is further characterized by data selected from one or more of the following: X-ray powder diffraction pattern having peaks at 12.4, 16.2, 17.2, 25.0 and 25.3 degrees two theta±0.1 degrees two theta and also having one, two, three or four peaks selected from: 8.1, 19.4, 22.0 and 23.3 degrees two theta±0.1 degrees two theta; an X-ray powder diffraction pattern having peaks at: 12.4, 16.2, 17.2, 25.0 and 25.3 degrees two theta±0.1 degrees two theta, absence of peaks at: 10.9 and 14.2 degrees two theta±0.2 degrees two theta and also having one, two, three or four peaks selected from: 8.1, 19.4, 22.0 and 23.3 degrees two theta±0.1 degrees two theta.

3B. A crystalline form E of Sofosbuvir according to paragraph 1B and/or 2B which is further characterized by the data set forth in following table:

| Angle (degrees two-theta |
|---|
| 8.1 |
| 10.4 |
| 12.1 |
| 12.4 |
| 13.5 |
| 16.2 |
| 16.8 |
| 17.2 |
| 18.0 |
| 18.7 |
| 19.4 |
| 20.1 |
| 20.9 |
| 22.0 |
| 23.3 |
| 23.7 |
| 24.4 |

4B. Crystalline form E of Sofosbuvir as defined in any of paragraphs 1B, 2B and/or 3B which is isolated.

5B. A process for preparing crystalline form E of Sofosbuvir as defined in any of paragraphs 1B, 2B, 3B and/or 4B comprising: combining Sofosbuvir with acetone and adding diisopropylether (DIPE).

6B. A process according to paragraph 4B wherein the Sofosbuvir and acetone are combined at a temperature of about room temperature (RT).

7B. A process according to paragraph 5B and/or 6B wherein after the addition of DIPE, the reaction mixture is maintained for about 48 h, preferably while stirring, at a temperature of about RT.

8B. A process according to any of paragraphs 5B, 6B and/or 7B further comprising filtering and drying steps.

9B. Use of a crystalline form E of Sofosbuvir according to any of paragraphs 1B, 2B, 3B and/or 4B for preparing a pharmaceutical composition and/or formulation.

10B. A crystalline form E of Sofosbuvir according to any of paragraphs 1B, 2B, 3B and/or 4B for use as a medicament, preferably for the treatment of Hepatitis C.

11B. A pharmaceutical composition or formulation comprising a crystalline form E of Sofosbuvir according to any of paragraphs 1B, 2B, 3B and/or 4B.

12B. A pharmaceutical composition according to paragraph 11B which is a solid composition and the Sofosbuvir retains its solid state form.

13B. A process for preparing a pharmaceutical composition or formulation according to paragraphs 11B and/or 12B comprising combining the crystalline form of Sofosbuvir according to any of paragraphs 1B, 2B, 3B and/or 4B with at least one pharmaceutically acceptable excipient.

14B. A method of treating a subject suffering from Hepatitis C, or otherwise in need of the treatment, comprising administration of an effective amount of a pharmaceutical composition comprising the crystalline form of Sofosbuvir according to any of paragraphs 1B, 2B, 3B and/or 4B.

1C. A crystalline form of Sofosbuvir, designated form E, characterized by data selected from one or more of the following: an X-ray powder diffraction pattern as depicted in FIG. 1; an X-ray powder diffraction pattern having peaks at: 12.4, 16.2, 17.2, 25.0 and 25.3 degrees two theta±0.1 degrees two theta; an X-ray powder diffraction pattern as depicted in FIG. 1; an X-ray powder diffraction pattern having peaks at: 12.4, 16.2, 17.2, 25.0 and 25.3 degrees two theta±0.1 degrees two theta and absence of peaks at: 10.9 and 14.2 degrees two theta±0.2 degrees two theta; and combinations of these data.

2C. A crystalline form E of Sofosbuvir according to paragraph 1C which is further characterized by data selected from one or more of the following: X-ray powder diffraction pattern having peaks at 12.4, 16.2, 17.2, 25.0 and 25.3 degrees two theta±0.1 degrees two theta and also having one, two, three or four peaks selected from: 8.1, 19.4, 22.0 and 23.3 degrees two theta±0.1 degrees two theta; an X-ray powder diffraction pattern having peaks at: 12.4, 16.2, 17.2, 25.0 and 25.3 degrees two theta±0.1 degrees two theta, absence of peaks at: 10.9 and 14.2 degrees two theta±0.2 degrees two theta and also having one, two, three or four peaks selected from: 8.1, 19.4, 22.0 and 23.3 degrees two theta±0.1 degrees two theta.

3C. A crystalline form E of Sofosbuvir according to any of paragraphs 1C and/or 2C which is further characterized by the data set forth in the following table:

| Angle (degrees two-theta) |
| --- |
| 8.1 |
| 10.4 |
| 12.1 |
| 12.4 |
| 13.5 |
| 16.2 |
| 16.8 |
| 17.2 |
| 18.0 |
| 18.7 |
| 19.4 |
| 20.1 |
| 20.9 |
| 22.0 |
| 23.3 |
| 23.7 |
| 24.4 |

4C. A monoclinic crystalline form of sofosbuvir, optionally according to any of paragraphs 1C, 2C and/or 3C, having space group $P2_1$ and having the following unit cell parameters a~14.47 Å, b~17.02 Å, c~5.22 Å, alpha~90.00°, beta~100.30° and gamma~90.00°, preferably as measured by synchrotron radiation at wavelength 0.40003 Å.

5C. A crystalline form of sofosbuvir according to any of paragraphs 1C, 2C, 3C and/or 4C, which is anhydrous.

6C. A crystalline form of Sofosbuvir according to any of paragraphs 1C, 2C, 3C, 4C, and/or 5C is isolated.

7C. A crystalline form of sofosbuvir according to any of paragraphs 1C, 2C, 3C, 4C, 5C and/or 6C, which is stable for at least 3 months at 40 degrees and at 25 degrees.

8C. A process for preparing crystalline form E of Sofosbuvir as defined in any of paragraphs 1C, 2C, 3C, 4C, 5C, 6C and/or 7C, comprising: combining Sofosbuvir with acetone and adding diisopropyl ether (DIPE).

9C. A process according to paragraph 8C wherein the Sofosbuvir and acetone are combined at a temperature of about room temperature (RT).

10C. A process according to paragraph 8C and/or 9C, wherein after the addition of DIPE, the reaction mixture is maintained for about 48 h, preferably while stirring, at a temperature of about RT.

11C. A process according to any of paragraphs 8C, 9C and/or 10C, further comprising filtering and drying steps.

12C. Use of a crystalline form E of Sofosbuvir according to any of paragraphs 1C, 2C, 3C, 4C, 5C, 6C and/or 7C for preparing a pharmaceutical composition and/or formulation.

13C. A crystalline form E of Sofosbuvir according to any of paragraphs 1C, 2C, 3C, 4C, 5C, 6C and/or 7C for use as a medicament, preferably for the treatment of Hepatitis C.

14C. A pharmaceutical composition or formulation comprising a crystalline form E of Sofosbuvir according to any of paragraphs 1C, 2C, 3C, 4C, 5C, 6C and/or 7C 15C. A pharmaceutical composition according to paragraph 14C which is a solid composition and the Sofosbuvir retains its solid state form.

16C. A process for preparing a pharmaceutical composition or formulation according to paragraphs 14C and/or 15C comprising combining the crystalline form of Sofosbuvir according to any of paragraphs 1C, 2C, 3C, 4C, 5C, 6C and/or 7C with at least one pharmaceutically acceptable excipient.

17C. A method of treating a subject suffering from Hepatitis C, or otherwise in need of the treatment, comprising administration of an effective amount of a pharmaceutical composition comprising a crystalline form of Sofosbuvir according to any of paragraphs 1C, 2C, 3C, 4C, 5C, 6C and/or 7C with at least one pharmaceutically acceptable excipient.

1D. A crystalline form of Sofosbuvir, designated form E, characterized by data selected from one or more of the following: an X-ray powder diffraction pattern as depicted in FIG. 1; an X-ray powder diffraction pattern having peaks at: 12.4, 16.2, 17.2, 25.0 and 25.3 degrees two theta±0.1 degrees two theta; an X-ray powder diffraction pattern as depicted in FIG. 1; an X-ray powder diffraction pattern having peaks at: 12.4, 16.2, 17.2, 25.0 and 25.3 degrees two theta±0.1 degrees two theta and absence of peaks at: 10.9 and 14.2 degrees two theta±0.2 degrees two theta; and combinations of these data.

2D. A crystalline form E of Sofosbuvir according to paragraph 1D which is further characterized by data selected from one or more of the following: X-ray powder diffraction pattern having peaks at 12.4, 16.2, 17.2, 25.0 and 25.3 degrees two theta±0.1 degrees two theta and also having one, two, three or four peaks selected from: 8.1, 19.4, 22.0 and 23.3 degrees two theta±0.1 degrees two theta; an X-ray powder diffraction pattern having peaks at: 12.4, 16.2, 17.2, 25.0 and 25.3 degrees two theta±0.1 degrees two theta, absence of peaks at: 10.9 and 14.2 degrees two theta±0.2 degrees two theta and also having one, two, three or four peaks selected from: 8.1, 19.4, 22.0 and 23.3 degrees two theta±0.1 degrees two theta.

3D. A crystalline form E of Sofosbuvir which is further characterized by the data set forth in the following table:

| Angle (degrees two-theta |
| --- |
| 8.1 |
| 10.4 |
| 12.1 |
| 12.4 |
| 13.5 |
| 16.2 |
| 16.8 |
| 17.2 |
| 18.0 |
| 18.7 |
| 19.4 |
| 20.1 |
| 20.9 |
| 22.0 |
| 23.3 |
| 23.7 |
| 24.4 |

4D. A monoclinic crystalline form of sofosbuvir, optionally according to any of paragraphs 1D, 2D and/or 3D having space group P2$_1$ and having the following unit cell parameters a~14.47 Å, b~17.02 Å, c~5.22 Å, alpha~90.00°, beta~100.30° and gamma-90.00°.

5D. A crystalline form of sofosbuvir according to any of paragraphs 1D, 2D, 3D and/or 4D, which is anhydrous.

6D. A crystalline form of sofosbuvir according to any of paragraphs 1D, 2D, 3D, 4D and/or 5D, which is isolated.

7D. A crystalline form of sofosbuvir according to any of paragraphs 1D, 2D, 3D, 4D, 5D and/or 6D, which is stable for at least 3 months at 40 degrees and at 25 degrees.

8D. A process for preparing crystalline form E of Sofosbuvir according to any of paragraphs 1D, 2D, 3D, 4D, 5D, 6D and/or 7D comprising: combining Sofosbuvir with acetone and adding diisopropyl ether (DIPE).

9D. A process according to paragraph 8D wherein the Sofosbuvir and acetone are combined at a temperature of about room temperature (RT).

10D. A process according to any of paragraphs 8D and/or 9D wherein after the addition of DIPE, the reaction mixture is maintained for about 48 h, preferably while stirring, at a temperature of about RT.

11D. A process according to any of paragraphs 8D, 9D and/or 10D, further comprising filtering and drying steps. The above described form of Sofosbuvir can be used to prepare a pharmaceutical compositions and formulations.

12D. Use of a crystalline form E of Sofosbuvir according to any of paragraphs 1D, 2D, 3D, 4D, 5D, 6D and/or 7D for preparing a pharmaceutical composition and/or formulation.

13D. A crystalline form E of Sofosbuvir according to any of paragraphs 1D, 2D, 3D, 4D, 5D, 6D and/or 7D for use as a medicament, preferably for the treatment of Hepatitis C.

14D. A pharmaceutical composition or formulation comprising a crystalline form E of Sofosbuvir according to any of paragraphs 1D, 2D, 3D, 4D, 5D, 6D and/or 7D.

15D. A pharmaceutical composition according to paragraph 14D which is a solid composition and the Sofosbuvir retains its solid state form.

16D. A process for preparing a pharmaceutical composition or formulation according to paragraphs 14D and/or 15D comprising combining the crystalline form of Sofosbuvir according to any of paragraphs 1D, 2D, 3D, 4D, 5D, 6D and/or 7D with at least one pharmaceutically acceptable excipient.

17D. A method of treating a subject suffering from Hepatitis C, or otherwise in need of the treatment, comprising administration of an effective amount of a pharmaceutical composition comprising a crystalline form of Sofosbuvir according to any of paragraphs 1D, 2D, 3D, 4D, 5D, 6D and/or 7D with at least one pharmaceutically acceptable excipient.

1E. Crystalline Sofosbuvir.

2E. Crystalline Sofosbuvir according to paragraph 1E, wherein the crystalline form is isolated.

3E. Crystalline Sofosbuvir according to paragraph 1E or 2E, wherein said Sofosbuvir is characterized by an X-ray powder diffraction pattern as depicted in FIG. 8.

4E. A solid state form of Sofosbuvir designated as Sofosbuvir Form 7 according to paragraphs 1E to 3E, characterized by data selected from one or more of the following X-ray powder diffraction pattern having peaks at 12.4, 13.5, 16.2, 25.3, and 27.2 degrees two theta±0.2 degrees two theta.

5E. A pharmaceutical composition comprising the crystalline or solid state form of Sofosbuvir according to any of the preceding paragraphs 1E-4E.

6E. A pharmaceutical formulation comprising the crystalline or solid state form of Sofosbuvir according to any of the preceding paragraphs 1E-4E, or the pharmaceutical composition of paragraph 5E, and at least one pharmaceutically acceptable excipient.

7E. Use of a crystalline or solid state form of Sofosbuvir of any one of paragraphs 1E to 4E for the preparation of pharmaceutical formulations of Sofosbuvir comprising one or more of the solid state forms thereof 8E. A process for preparing the pharmaceutical formulation according to paragraph 6E comprising combining the crystalline or solid state form of Sofosbuvir according to any of the preceding paragraphs 1E-4E, or the pharmaceutical composition according to paragraph 5E, with at least one pharmaceutically acceptable excipient.

9E. The crystalline or solid state form of Sofosbuvir according to any of the preceding paragraphs 1E-4E, the pharmaceutical composition of paragraph 5E, or the pharmaceutical formulation according to paragraph 6E for use as a medicament.

10E. The crystalline or solid state form of Sofosbuvir according to any of the preceding paragraphs 1E-4E, the pharmaceutical composition according to paragraph 5E, or the pharmaceutical formulation according to paragraph 6E for use in treating a subject suffering from Hepatitis C.

11E. A method of treating a subject suffering from Hepatitis C, comprising administering a therapeutically effective amount of the crystalline or solid state form of Sofosbuvir according to any of the preceding paragraphs 1E-4E, the pharmaceutical composition according to paragraph 5E, or the pharmaceutical formulation according to paragraph 6E.

1F. Crystalline Form 7 of Sofosbuvir characterised by an X-ray powder diffraction pattern having one or more peaks at about: 12.4, 13.5, 16.2, 25.3, and 27.2±0.2 degrees two theta.

2F. Crystalline Form 7 Sofosbuvir according to paragraph 1F characterised by an X-ray powder diffraction pattern having two, three, four or five peaks at about: 12.4, 13.5, 16.2, 25.3, and 27.2±0.2 degrees two theta.

3F. Crystalline Form 7 Sofosbuvir according to paragraph 1F or paragraph 2F characterised by an X-ray powder diffraction pattern having peaks at about: 12.4, 13.5, 16.2, 25.3, and 27.2±0.2 degrees two theta.

4F. Crystalline Form 7 of Sofosbuvir according to any of paragraphs 1F-3F further having characteristic X-ray powder diffraction pattern with one or more peaks at about: 8.1, 10.4, 17.2, 19.4, and 20.9±0.2 degrees two theta.

5F. Crystalline Form 7 of Sofosbuvir according to any of paragraphs 1F-4F further having characteristic X-ray powder diffraction pattern with two, three, four or five peaks at about: 8.1, 10.4, 17.2, 19.4, and 20.9±0.2 degrees two theta.

6F. Crystalline Form 7 of Sofosbuvir according to any of paragraphs 1F-5F further having characteristic X-ray powder diffraction pattern with peaks at about: 8.1, 10.4, 17.2, 19.4, and 20.9±0.2 degrees two theta.

7F. Crystalline Form 7 of Sofosbuvir according to any of paragraphs 1F-6F characterised by an X-ray powder diffraction pattern having peaks at about: 8.1, 10.4, 12.4, 13.5, 16.2, 17.2, 19.4, 20.9, 25.3, and 27.2±0.2 degrees two theta.

8F. Crystalline Form 7 of Sofosbuvir according to any of paragraphs 1F-7F characterised by: the XRPD peak listings in the first column of the table in FIG. 11, the XRPD peak listings in the table in FIG. 11 including the intensities, or an X-ray powder diffraction pattern substantially as depicted in FIG. 10.

9F. Crystalline Form 7 of Sofosbuvir characterised by having lattice parameters at T=120 K substantially as follows:

| | |
|---|---|
| Cell length a: | 5.17 Å |
| Cell length b: | 16.85 Å |
| Cell length c: | 14.44 Å |
| Cell angle alpha: | 90° |
| Cell angle beta: | 100.2° |
| Cell angle gamma: | 90° |

10F. Crystalline Form 7 of Sofosbuvir according to paragraph 9F further characterised by data according to any of Paragraphs 1F-8F.

11F. Crystalline Form 7 Sofosbuvir according to any of paragraphs 1F-10F in the form of rod-shaped crystals.

12F. Crystalline Form 7 Sofosbuvir according to any of paragraphs 1F-11F having a particle size distribution $D_{10} \geq 4$ μm as measured by laser diffractometry.

13F. Crystalline Form 7 Sofosbuvir according to any of paragraphs 1F-12F having a $D_{50}$ particle size distribution selected from: ≥about 25 μm, about 15 to about 300 μm, about 20 to about 250 μm, about 20 to about 200 μm, about 20 to about 150 μm, about 20 to about 75 μm, or about 25 to about 50 μm, as measured by laser diffractometry.

14F. Crystalline Form 7 Sofosbuvir according to any of paragraphs 1F-13F having a $D_{90}$ particle size distribution selected from ≥about 75 μm, about 50 to about 500 μm, about 60 to about 400 μm, about 75 to about 300 μm, about 75 to about 200 μm, or about 75 to about 150 μm, as measured by laser diffractometry.

15F. Crystalline Form 7 Sofosbuvir according to any of paragraphs 1F-14F which is substantially free of any other crystalline form of Sofosbuvir.

16F. Use of crystalline Form 7 Sofosbuvir as defined in any of paragraphs 1F-15F for the preparation of a pharmaceutical composition.

17F. A pharmaceutical composition comprising crystalline Form 7 Sofosbuvir as defined in any of paragraphs 1F-15F.

18F. A pharmaceutical composition according to paragraph 17F further comprising at least one pharmaceutically acceptable excipient.

19F. Crystalline Form 7 Sofosbuvir as defined in any of paragraphs 1F-15F for use as a medicament.

20F. Crystalline Form 7 Sofosbuvir according to paragraph 19F for use in the treatment of Hepatitis C.

21F. A method of treating a subject suffering from Hepatitis C, comprising administering a therapeutically effective amount of the crystalline form of Sofosbuvir as defined in any of paragraphs 1F-15F, or a pharmaceutical composition thereof as defined in any of paragraphs 17F-18F.

22F. A process for preparing Sofosbuvir crystalline form 7 comprising:
(a) contacting Sofosbuvir with a solvent system comprising water and an organic solvent,
(b) allowing the mixture to stand for a period of time sufficient to form Sofosbuvir crystalline form 7, and optionally
(c) isolating the Sofosbuvir crystalline form 7.

23F. A process according to paragraph 22F wherein the organic solvent is not freely miscible with water.

24F. A process according to paragraph 23F wherein the organic solvent has a water miscibility at room temperature such that water is soluble in the organic solvent at concentrations of from about 0.1 to about 20% (w/w), about 0.1 to about 10% (w/w), about 0.2 to about 5% (w/w), about 0.5 to about 5% (w/w), about 0.5 to about 5% (w/w) or about 1 to about 3% (w/w).

25F. A process according to paragraph 24F wherein the organic solvent has a water miscibility such that water is soluble in the organic solvent at concentrations about 0.5 to about 5 wt %, about 0.5 to about 5 wt % or about 1 to about 3 wt %.

26F. A process according to any of paragraphs 24F-25F wherein the organic solvent is selected from the group consisting of: aliphatic ethers, cyclic ethers, ketones, alcohols and esters.

27F. A process according to paragraph 26F wherein the organic solvent is selected from the group consisting of: $C_{4-8}$ dialkyl ether, $C_{1-3}$ alkyl-substituted $C_{4-8}$ cyclic ether, $C_{4-8}$ ketone, $C_{4-8}$ aliphatic alcohol and $C_{1-4}$ alkyl ester of $C_{4-8}$ alcohol.

28F. A process according to paragraph 27F wherein the organic solvent is selected from the group consisting of: $C_{4-6}$ alkyl ether, $C_{1-3}$ alkyl-substituted $C_{4-6}$ cyclic ether, $C_{4-6}$ ketone, $C_{4-6}$ aliphatic alcohol and $C_{1-3}$ alkyl ester of $C_{4-6}$ alcohol.

29F. A process according to any of paragraphs 22F-28F wherein the organic solvent is selected from the group consisting of: diethyl ether, dipropyl ether, diisopropyl-ether, dibutyl ether, tert-amyl methyl ether, methyl tert-butyl ether, methyl isopropyl ether, 2-methyltetrahydrofuran, ethyl tert-butyl ether, methyl isobutyl ketone, diethyl ketone, methyl butyl ketone, isoamyl alcohol, ethyl acetate, and n-butyl acetate.

30F. A process according to any of paragraphs 22F-29F wherein the solvent system is a water-saturated organic solvent.

31F. A process according to any of paragraphs 22F-30F wherein the organic solvent is selected from the group consisting of $C_{4-8}$ dialkyl ether or $C_{1-3}$ alkyl-substituted $C_{4-8}$ cyclic ether, and preferably a $C_{4-8}$ dialkyl ether.

32F. A process according to any of paragraphs 22F-31F wherein the solvent system is a mixture of methyl tert-butyl ether and water.

33F. A process according to any of paragraphs 22F-32F wherein the solvent system is water-saturated methyl tert-butyl ether.

34F. A process according to any of paragraphs 22F-33F wherein the solvent system is methyl tert-butyl ether containing about 0.5 to about 3 wt %, about 0.8 to about 2 wt % or about 1 to about 1.5 wt % water.

35F. A process according to any of paragraphs 22F-34F wherein the solvent system is prepared by a process comprising stirring the organic solvent with a sufficient excess of water to form a biphasic mixture, and discarding the aqueous phase.

36F. A process according to paragraph 35F wherein the solvent system is prepared by a process comprising stirring methyl tert-butyl ether with water in a volume ratio of MTBE:water of from: about 5:1 to about 25:1, about 5:1 to about 20:1, about 5:1 to about 15:1, about 8:1 to about 12:1, or about 10:1, and discarding the aqueous phase.

37F. A process according to any of paragraphs 22F-36F, wherein the amount of solvent system per gram of Sofosbuvir is from about 5 ml to about 25 ml, about 5 ml to about 20 ml, about 10 ml to about 20 ml, about 12 ml to about 18 ml, or about 15 to about 16 ml.

38F. A process according to any of paragraphs 22F-37F wherein the mixture is allowed to stand at a temperature of from: about 10° C. to about 80° C., about 15° C. to about 60° C., about 15° C. to about 40° C., about 18 to about 30° C., or about 20 to about 25° C.

39F. A process according to any of paragraphs 22F-38F wherein the mixture formed in step (a) is filtered prior to step (b).

40F. A process according to any of paragraphs 22F-39F wherein the mixture in step (b) is seeded with crystalline Sofosbuvir form 7.

41F. A process according to any of paragraphs 22F-40F wherein the mixture is allowed to stand for about 12 to about 96 hours, about 18 to about 60 hours, or about 30-50 hours.

42F. A process according to any of paragraphs 22F-41F wherein the mixture is allowed to stand without stirring, preferably in a closed vessel.

43F. A process according to any of paragraphs 22F-42F wherein the Sofosbuvir starting material in step (a) is crystalline Form 1.

44F. A process according to any of paragraphs 22F-43F wherein after isolating the Sofosbuvir crystalline form 7, the product is dried under vacuum.

45F. A process according to paragraph 44F wherein the drying is carried out at a temperature of about 18° C. to about 30° C., about 20° C. to about 25° C., or at room temperature.

46F. Sofosbuvir crystalline form 7 prepared by the process of any of paragraphs 22F-45F.

47F. A process according to any of paragraphs 22F-45F further comprising combining the Sofosbuvir crystalline form 7 with one or more pharmaceutically acceptable excipients to form a pharmaceutical composition thereof 48F. A pharmaceutical composition comprising Sofosbuvir crystalline form 7 prepared by the process of paragraph 47F.

1G. Pharmaceutical composition comprising small particle size sofosbuvir and no glidants.

2G. The pharmaceutical composition of paragraph 1G, wherein the composition comprises not more than 1.5% of lubricants based on the weight of the total composition.

3G. The pharmaceutical composition of paragraph 1G or 2G, wherein the small particle size sofosbuvir has a d(0.5) of less than 20 μm, preferably less than 10 μm, more preferably less than 5 μm and most preferably between 1-2 μm.

4G. The pharmaceutical composition of any of paragraphs 1G-3G, wherein the small particle size sofosbuvir has a d(0.1) of 0.4-0.6 μm, a d(0.5) of 1.0-2.0 μm and a d(0.9) of 3.2-5.0 μm.

5G. Pharmaceutical composition of any of paragraphs 1G-4G, wherein the small particle size sofosbuvir is present in crystalline form.

6G. The pharmaceutical composition of paragraph 5G, wherein the crystalline sofosbuvir has an X-ray powder diffraction pattern comprising peaks at 12.4, 16.2, 17.2, 25.0 and 25.3 degrees two theta±0.1 degrees two theta, and preferably peaks at 10.9 and 14.2 degrees two theta±0.2 degrees two theta are absent in the X-ray powder diffraction pattern.

7G. The pharmaceutical composition of paragraph 5G, wherein the small particle size sofosbuvir is sofosbuvir of form 6.

8G. The pharmaceutical composition of paragraph 5G, wherein the small particle size sofosbuvir is sofosbuvir of form E.

9G. The pharmaceutical composition of paragraph 8G, wherein the composition is a solid pharmaceutical composition and the sofosbuvir is contained in an amount of 35 to 75%, based on the total weight of the composition, preferably in an amount of 40-50% based on the total weight of the composition.

10G. The pharmaceutical composition of any of paragraphs 1G-9G, wherein the composition is in form of a tablet comprising one or more pharmaceutically acceptable excipients.

11G. The pharmaceutical composition of paragraph 10G, wherein the sofosbuvir is contained in an amount of 35 to 75%, based on the total weight of the tablet, preferably in an amount of 40-50% based on the total weight of the tablet.

12G. The pharmaceutical composition of paragraphs 10G or 11G, wherein the tablet contains the sofosbuvir as sole active ingredient in an amount of 35 to 55%, based on the total weight of the tablet.

13G. The pharmaceutical composition of any of paragraphs 10G-12G, wherein the tablet contains one or more disintegrants and the relative amount of disintegrants in the composition is more than 10%, preferably more than 12% by weight based on the weight of the total composition.

14G. The pharmaceutical composition of any of paragraphs 10G-13G, wherein the tablet contains about 400 mg sofosbuvir and wherein preferably the total tablet weight is not more than 1020 mg.

15G. The pharmaceutical composition of any of paragraphs 10G-14G, wherein the tablet contains one or more binders and one or more disintegrants.

16G. The pharmaceutical composition of any of paragraphs 1G-15G for use in the treatment of hepatitis C virus infections.

17G. Process for preparing pharmaceutical compositions in the form of a tablet according to any of paragraphs 10G-15G comprising the process steps wherein the active ingredient and the one or more pharmaceutically acceptable excipients are compacted, the compacted mass is crushed, optionally sieved and compressed to the pharmaceutical composition in the form of a tablet according to any of paragraphs 10G-15G.

The invention claimed is:

1. A process for preparing Sofosbuvir crystalline form 7 comprising:
   (a) contacting Sofosbuvir with a solvent system comprising methyl tert-butyl ether containing 0.5-3 wt %, 0.8-2%, or 1-1.5 wt % water,
   (b) allowing the mixture to stand for a period of time sufficient to form Sofosbuvir crystalline form 7, and optionally
   (c) isolating the Sofosbuvir crystalline form 7.

2. The process of claim 1, further comprising preparing the solvent system by a process comprising stirring the methyl tert-butyl ether (MTBE) with water in a volume ratio of MTBE:water of from: 5:1 to 25:1, 5:1 to 20:1, 5:1 to 15:1, 8:1 to 12:1, or about 10:1, and discarding the aqueous phase.

3. The process of claim 1, wherein the mixture is allowed to stand without stirring, optionally in a closed vessel.

4. The process of claim 1, wherein the Sofosbuvir crystalline form 7 in step (c) is characterised by one or more of the following:
   (i) an X-ray powder diffraction pattern having peaks at: 12.4, 13.5, 16.2, 25.3, and 27.2±0.2 degrees two theta, and optionally further peaks at: 8.1, 10.4, 17.2, 19.4, and 20.9±0.2 degrees two theta, or
   (ii) X-ray powder diffraction peaks at the 2-theta values in FIG. 3 optionally with the corresponding intensities, or
   (iii) an X-ray powder diffraction pattern substantially as depicted in FIG. 1; or
   (iv) crystal lattice parameters substantially as follows:

| | |
|---|---|
| Cell length a: | 5.17 Å |
| Cell length b: | 16.85 Å |
| Cell length c: | 14.44 Å |

-continued

| | |
|---|---|
| Cell angle alpha: | 90° |
| Cell angle beta: | 100.2° |
| Cell angle gamma: | 90° |
| as determined by single crystal analysis. | |

5. The process according to claim 4, wherein the Sofosbuvir crystalline form 7 in step (c) is further characterised by one or more of the following:
   (v) a $D_{10}$ particle size distribution $D_{10}$>4 μm as measured by laser diffractometry,
   (vi) a $D_{50}$ particle size distribution selected from: >25 μm, 15 to 300 μm, 20 to 250 μm, 20 to 200 μm, 20 to 150 μm, 20 to 75 μm, or 25 to 50 μm, as measured by laser diffractometry; or
   (vii) a $D_{90}$ particle size distribution selected from >75 μm, 50 to 500 μm, 60 to 400 μm, 75 to 300 μm, s 75 to 200 μm, or 75 to 150 μm, as measured by laser diffractometry.

6. Small particle size or micronized crystalline form E of sofosbuvir, having a particle size distribution (PSD) of d(0.1) 0.4-0.6 microns, d(0.5) 1.0-2.0 microns and d(0.9) 3.2-5.0 microns.

7. The small particle size or micronized crystalline form E of sofosbuvir of claim 6, exhibiting a flow rate of not more than 100 sec/100 g, not more than 80 sec/100 g, or not more than 65 sec/100 g, as measured by flow-to-an-orifice in Pharma Test 41-03300 automated powder testing system.

8. The small particle size or micronized crystalline form E of sofosbuvir of claim 6, exhibiting a constant density of not less than 0.4 g/ml, not less than 0.43 g/ml, or not less than 0.48 g/ml as measured at 0.2 MPa.

9. The small particle size or micronized crystalline form E of sofosbuvir of claim 6, having a water sorption of not more than 0.5% or not more than 0.3%, as measured by dynamic vapour sorption, and water content after equilibration at 90% RH.

10. The small particle size or micronized crystalline form E of sofusbuvir according to claim 6, having a flow rate of not more than 65 sec/100 g, a constant density of not less than 0.48 g/m; as measured at 0.2 MPa, and a water sorption of not more than 0.3% as measured by DVS and water content after equilibrium at 90% RH.

11. The small particle size or micronized crystalline form E according to claim 6, wherein the Form E of sofosbuvir is characterised by data selected from one or more of the following:
   an X-ray powder diffraction pattern having peaks at: 12.4, 16.2, 17.2, 25.0 and 25.3 degrees two theta±0.1 degrees two theta;
   an X-ray powder diffraction pattern as depicted in FIG. 1 or FIG. 7;
   an X-ray powder diffraction pattern having peaks at: 12.4, 16.2, 17.2, 25.0 and 25.3 degrees two theta±0.1 degrees two theta and absence of peaks at: 10.9 and 14.2 degrees two theta±0.2 degrees two theta,
   and combinations of these data.

12. The small particle size or micronized crystalline form E according to claim 6, wherein the Form E of sofosbuvir is further characterised by data selected from one or more of the following:
   X-ray powder diffraction pattern having peaks at 12.4, 16.2, 17.2, 25.0 and 25.3 degrees two theta±0.1 degrees two theta and also having one, two, three or four peaks selected from: 8.1, 19.4, 22.0 and 23.3 degrees two theta±0.1 degrees two theta;

an X-ray powder diffraction pattern having peaks at: 12.4, 16.2, 17.2, 25.0 and 25.3 degrees two theta±0.1 degrees two theta, absence of peaks at: 10.9 and 14.2 degrees two theta±0.2 degrees two theta and also having one, two, three or four peaks selected from: 8.1, 19.4, 22.0 and 23.3 degrees two theta±0.1 degrees two theta.

13. A process for preparing crystalline Form E of Sofosbuvir comprising:
(a) combining Sofosbuvir with water and an organic solvent that is methyl-t-butyl ether, t-butanol, acetone, or methyl isobutyl ketone to form a mixture, wherein the amount of water is 0.5-2% by volume,
(b) optionally seeding the mixture with a crystalline form E of sofosbuvir,
(c) adding an organic anti-solvent that is di-iso-propyl ether, heptane, hexane, or cyclohexane to form a second mixture,
(d) allowing the second mixture to stand for a period of time sufficient to form Sofosbuvir crystalline form E; and
(e) isolating the crystalline Sofosbuvir form E.

14. The process of claim 13, wherein the organic solvent is methyl isobutyl ketone.

15. The process of claim 14 wherein the organic anti-solvent is cyclohexane.

16. The process of claim 13, wherein the organic solvent is acetone.

17. The process of claim 13, wherein the organic anti-solvent is diisopropyl ether, n-heptane, or cyclohexane.

18. The process of claim 13, carried out at temperatures of between 0° C. and 20° C., 0° C. to 15° C., or 6° C. to 12° C.

19. The process of claim 13, performed with stirring.

20. The process of claim 13, wherein the amount of water combined with the organic solvent is 1% by volume.

21. The process of claim 13, further comprising a step of milling, micronizing, or delumping.

22. The process of claim 13, wherein the water is combined with an organic solvent that is methyl isobutyl ketone to form a mixture wherein the amount of water is 1% by volume and the temperature is 9±3° C.; and wherein the organic anti-solvent is cyclohexane.

23. The process of claim 13, wherein the crystalline Sofosbuvir Form E is characterized by data selected from one or more of the following:
an X-ray powder diffraction pattern having peaks at: 12.4, 16.2, 17.2, 25.0 and 25.3 degrees two theta±0.1 degrees two theta;
an X-ray powder diffraction pattern as depicted in FIG. 1 or FIG. 7;
an X-ray powder diffraction pattern having peaks at: 12.4, 16.2, 17.2, 25.0 and 25.3 degrees two theta±0.1 degrees two theta and absence of peaks at: 10.9 and 14.2 degrees two theta±0.2 degrees two theta,
and combinations of these data;
and optionally further characterized by selected from one or more of the following:
X-ray powder diffraction pattern having peaks at 12.4, 16.2, 17.2, 25.0 and 25.3 degrees two theta±0.1 degrees two theta and also having one, two, three or four peaks selected from: 8.1, 19.4, 22.0 and 23.3 degrees two theta±0.1 degrees two theta;
an X-ray powder diffraction pattern having peaks at: 12.4, 16.2, 17.2, 25.0 and 25.3 degrees two theta±0.1 degrees two theta, absence of peaks at: 10.9 and 14.2 degrees two theta±0.2 degrees two theta, and also having one, two, three or four peaks selected from: 8.1, 19.4, 22.0 and 23.3 degrees two theta±0.1 degrees two theta.

24. The process of claim 13, wherein the organic anti-solvent is cyclohexane.

* * * * *